United States Patent
Heeres et al.

(10) Patent No.: US 9,650,348 B2
(45) Date of Patent: May 16, 2017

(54) TRIAZINES WITH SUITABLE SPACERS FOR TREATMENT AND/OR PREVENTION OF HIV INFECTIONS

(71) Applicants: Universiteit Antwerpen, Antwerpen (BE); Shakturana CV, Turnhout (BE); Jan Heeres, Vosselaar (BE)

(72) Inventors: Jan Heeres, Vosselaar (BE); Koen Augustyns, Wilrijk (BE); Pieter Van Der Veken, Sint-Katelijne Waver (BE); Jurgen Joossens, Zoersel (BE); Venkatraj Muthusamy, Wilrijk (BE); Kevin Karel Florentina Arien, Antwerpen (BE); Guido Louis Emile Vanham, Antwerpen (BE); Paulus Lewi

(73) Assignees: Universiteit Antwerpen, Antwerp (BE); Shakturana CV, Turnhout (BE); Jan Heeres, Vosselaar (BE)

( * ) Notice: Subject to any disclaimer, the term of this patent is extended or adjusted under 35 U.S.C. 154(b) by 0 days.

(21) Appl. No.: 14/385,843

(22) PCT Filed: Mar. 18, 2013

(86) PCT No.: PCT/EP2013/055525
§ 371 (c)(1),
(2) Date: Sep. 17, 2014

(87) PCT Pub. No.: WO2013/139727
PCT Pub. Date: Sep. 26, 2013

(65) Prior Publication Data
US 2015/0126510 A1     May 7, 2015

(30) Foreign Application Priority Data
Mar. 19, 2012  (GB) .................................. 1204756.9

(51) Int. Cl.
*C07D 251/70* (2006.01)
*C07D 251/52* (2006.01)
*A61K 31/53* (2006.01)
*A61P 31/18* (2006.01)
*A61K 31/18* (2006.01)

(52) U.S. Cl.
CPC ............ *C07D 251/70* (2013.01); *A61K 31/18* (2013.01); *A61K 31/53* (2013.01); *C07D 251/52* (2013.01)

(58) Field of Classification Search
CPC .. C07D 251/54; C07D 251/48; C07D 251/26; A61K 31/53
USPC .......................... 544/197, 208, 219; 514/245
See application file for complete search history.

(56) References Cited

PUBLICATIONS

Sultan et al. HIV/AIDS—Research and Palliative Care 2014:6 147-158.*
Freshney et al., Culture of Animal Cells, A Manual of Basic Techniques, Alan R. Liss, Inc., 1983, New York, p. 4.*
Dermer et al., Bio/Technology, 1994, 12:320.*
Wolff Manfred E. "Burger's Medicinal Chemistry, 5ed, Part 1", John Wiley & Sons, 1995, pp. 975-977.*
Banker, G.S. et al, "Modern Pharmaceutics, 3ed.", Marcel Dekker, New York. 1996, pp. 451 and 596.*
International Search Report Pertaining to Application No. PCT/EP2013/055525 with a filing date of Mar. 18, 2013.
Search Report Pertaining to Application No. GB1204756.9 with a filing date of Mar. 19, 2012.

* cited by examiner

*Primary Examiner* — Venkataraman Balasubramanian
(74) *Attorney, Agent, or Firm* — Dinsmore & Shohl LLP

(57) ABSTRACT

The present invention relates to the field of HIV-1 infections, and in particular provides novel compounds containing triazine rings and suitable spacers. The compounds according to this invention are very suitable for the prevention and/or treatment of HIV-1 infection and in particular show improved activity against NNRTI-resistant viruses of HIV-1.

11 Claims, No Drawings

TRIAZINES WITH SUITABLE SPACERS FOR TREATMENT AND/OR PREVENTION OF HIV INFECTIONS

FIELD OF THE INVENTION

The present invention relates to the field of HIV-1 infections, and in particular provides novel compounds containing triazine rings and suitable spacers. The compounds according to this invention are very suitable for the prevention and/or treatment of HIV-1 infection and in particular show improved activity against NNRTI-resistant viruses of HIV-1.

BACKGROUND TO THE INVENTION

Acquired immune deficiency syndrome (AIDS) is caused by the human immunodeficiency virus type-1 (HIV-1). When HIV-1 infects a cell, reverse transcriptase copies the viral single stranded RNA genome into a double-stranded viral DNA. The viral DNA is then integrated into the host chromosomal DNA, which then allows host cellular processes, such as transcription and translation to reproduce the virus. RTIs (reverse transcriptase inhibitors) block reverse transcriptase's enzymatic function and prevent completion of synthesis of the double-stranded viral DNA, thus preventing HIV from multiplying.

In the current treatment of HIV-1 infections, non-nucleoside reverse transcriptase inhibitors (NNRTIs) are very important in particular in drug combination therapies (highly active antiretroviral therapy or HAART) due to their unique antiviral activity. However, while NNRTIs (non-nucleoside reverse-transcriptase inhibitors) are effective at inhibiting DNA synthesis and HIV replication, HIV can develop mechanisms that confer the virus resistance to the drugs. HIV-1 reverse transcriptase does not have proof-reading activity, and this property combined with selective pressure from the drug inhibitors can lead to mutations in reverse transcriptase which makes the virus less susceptible to NNRTIs.

NNRTIs do not bind to the active site of the polymerase but in a less conserved pocket near the active site in the p66 subdomain. Their binding results in a conformational change in the reverse transcriptase that distorts the positioning of the residues, inhibiting polymerization. Mutations in response to first generation NNRTIs decrease the binding of these drugs in the pocket. There are three main mechanisms of NNRTI resistance:

a) the first NNRTI mutations disrupting the entry of the inhibitor to the NNRTI binding pocket is exemplified by the K103N and K101E mutations located at the entrance of the pocket, blocking the entrance/binding of the old generation drug in contrast to new generation drugs.

b) A second mechanism is the loss of important interactions on the inside of the pocket, exemplified by Y181C and Y188C mutations resulting in the loss of important π-π interactions between aromatic rings of the substrate and enzyme involved in NNRTI binding.

c) The third type of mutations can be involved in the size of the NNRTI binding pocket, creating a steric bulk in the pocket, leaving less room for an NNRTI to bind tightly, an example is the G190E mutation.

Exemplary NNRTIs are diaryltriazines (DATA) (1-6) which are very potent NNRTIs and have anti-HIV-1 activity with nanomolar $EC_{50}$ values against wild-type and single mutants. However, a problem with said prior art known DATA's is that they are less active or even ineffective against double and multiple HIV-1 mutants (1).

We have now discovered that by making use of suitable spacers in diaryltriazines, the compounds show an improved activity against double and multiple mutants compared to the corresponding triazines without spacer and prior art known diarylpyrimidines such as compound TMC120 (DAPY, Diarylpyrimidines). Dose-escalation studies making use of the compounds of the present application have shown a distinct mutational profile in comparison to NNRTI's, which are currently used in clinical management of HIV infection. This distinct mutational profile may potentially result in a clinical benefit since available therapy would not be compromised. This aspect makes this invention an important improvement compared to the current state of the art.

The present invention discloses compounds which differ from prior art compounds in structure and/or pharmacological activity.

SUMMARY OF THE INVENTION

The invention is based on novel compounds, which contain triazine rings with suitable spacers. Surprisingly, the novel compounds of this present invention showed improved activity against NNRTI-resistant viruses of HIV-1.

Viewed from a first aspect, the invention provides a compound of Formula (Ia) or (Ib) or a stereoisomer, tautomer, racemic, metabolite, pro- or predrug, salt, hydrate, or solvate thereof,

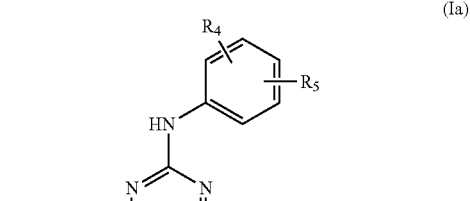

(Ia)

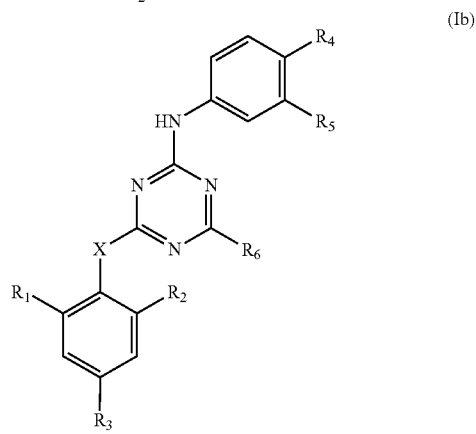

(Ib)

Wherein $R_1$, $R_2$, and $R_3$ are each independently selected from the list comprising —$C_{1-6}$alkyl, -halo, and —CH=CH—CN;

$R_4$ and $R_5$ are each independently selected from the list comprising —H, —CN, and —CH=CH—CN;

$R_6$ is selected from the list comprising —H, and —$NR_7R_8$;

$R_7$ and $R_8$ are each independently selected from the list comprising —H, —$C_{1-6}$alkyl, and -phenyl; said -phenyl being optionally substituted with —CN; or $R_7$ and $R_8$ taken together with the N atom to which they are attached form a 5- or 6-membered heterocycle comprising from 1 to 3 heteroatoms selected from N, S and O;

X is selected from the list comprising —NH—, —$NC_{1-6}$alkyl-, —O—; and wherein at least one or $R_1$-$R_5$ is —CH=CH—CN In a particular embodiment, this invention provides a compound of formula (Ia) or (Ib) wherein $R_1$ and $R_2$ are each independently selected from the list comprising —$C_{1-6}$alkyl, and -halo;

$R_3$ is —CH=CH—CN;

$R_4$ and $R_5$ are each independently selected from the list comprising —H, and —CN;

$R_6$ is selected from the list comprising —H, and —$NR_7R_8$;

$R_7$ and $R_8$ are each independently selected from the list comprising —H, —$C_{1-6}$alkyl, and -phenyl; said -phenyl being optionally substituted with —CN; or $R_7$ and $R_8$ taken together with the N atom to which they are attached form a 5- or 6-membered heterocycle comprising from 1 to 3 heteroatoms selected from N, S and O;

X is selected from the list comprising —NH—, —$NC_{1-6}$alkyl-, —O—.

In another particular embodiment, this invention provides a compound of formula (Ia) or (Ib) wherein $R_1$, $R_2$, and $R_3$ are each independently selected from the list comprising —$C_{1-6}$alkyl, -halo, and —CH=CH—CN;

$R_4$ and $R_5$ are each independently selected from the list comprising —H, and —CN;

$R_6$ is —$NR_7R_8$;

$R_7$ and $R_8$ are each independently selected from the list comprising —H, —$C_{1-6}$alkyl, and -phenyl; said -phenyl being optionally substituted with —CN; or $R_7$ and $R_8$ taken together with the N atom to which they are attached form a 5- or 6-membered heterocycle comprising from 1 to 3 heteroatoms selected from N, S and O;

X is selected from the list comprising —NH—, —$NC_{1-6}$alkyl-, —O—; and wherein at least one or $R_1$-$R_3$ is —CH=CH—CN In yet another particular embodiment, this invention provides a compound of formula (Ia) or (Ib) wherein $R_1$ and $R_2$ are each independently selected from the list comprising —$C_{1-6}$alkyl, and -halo;

$R_3$ is —CH=CH—CN;

$R_4$ and $R_5$ are each independently selected from the list comprising —H, —CN, and —CH=CH—CN;

$R_6$ is —$NR_7R_8$;

$R_7$ and $R_8$ are each independently selected from the list comprising —H, —$C_{1-6}$alkyl, and -phenyl; said -phenyl being optionally substituted with —CN; or $R_7$ and $R_8$ taken together with the N atom to which they are attached form a 5- or 6-membered heterocycle comprising 1 to 3 heteroatoms selected from N, S and O;

X is selected from the list comprising —NH—, —$NC_{1-6}$alkyl-, —O—

In further embodiment, this invention provides a compound of formula (Ia) or (Ib) wherein $R_1$ and $R_2$ are each independently selected from the list comprising —$C_{1-6}$alkyl, and -halo;

$R_3$ is —CH=CH—CN;

$R_4$ is —CN;

$R_5$ is —H;

$R_6$ is —$NR_7R_8$;

$R_7$ and $R_8$ are each independently selected from the list comprising —H and —$C_{1-6}$alkyl;

X is selected from the list comprising —NH— and —O—

In particular, the compound according to the present invention is the E-isomer of said compound.

In a further aspect, this invention provides a pharmaceutical composition comprising a compound according to this invention suitable for use as a human or veterinary medicine.

This invention further provides a compound or a composition according to this invention, for use as a medicament.

This invention in particular provides a compound or composition according to this invention, for use in the prevention and/or treatment of HIV infections in a subject in need thereof.

In yet a further aspect, this invention provides the use of a compound or composition according to this invention as a non-nucleoside reverse transcriptase inhibitor.

In a final aspect this invention provides a method for the prevention and/or treatment of HIV infections; said method comprising administering to a subject in need thereof a compound or a composition according to this invention.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

As already mentioned hereinbefore, in a first aspect the present invention provides compounds of Formula (Ia) or (Ib), or a stereoisomer, tautomer, racemic, metabolite, pro- or predrug, salt, hydrate, N-oxide form, or solvate thereof,

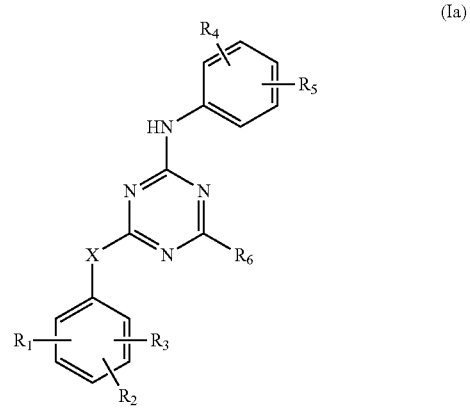

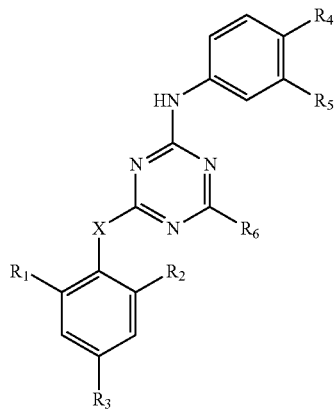

Wherein
$R_1$, $R_2$, and $R_3$ are each independently selected from the list comprising —$C_{1-6}$alkyl, -halo, and —CH=CH—CN;
$R_4$ and $R_5$ are each independently selected from the list comprising —H, —CN, and —CH=CH—CN;
$R_6$ is selected from the list comprising —H, and —$NR_7R_8$;
$R_7$ and $R_8$ are each independently selected from the list comprising —H, —$C_{1-6}$alkyl, and -phenyl; said -phenyl being optionally substituted with —CN; or
$R_7$ and $R_8$ taken together with the N atom to which they are attached form a 5- or 6-membered heterocycle comprising from 1 to 3 heteroatoms selected from N, S and O;
X is selected from the list comprising —NH—, —$NC_{1-6}$alkyl-, —O—; and
wherein at least one or $R_1$-$R_5$ is —CH=CH—CN When describing the compounds of the invention, the terms used are to be construed in accordance with the following definitions, unless a context dictates otherwise:

The term "alkyl" by itself or as part of another substituent refers to fully saturated hydrocarbon radicals. Generally, alkyl groups of this invention comprise from 1 to 6 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl means an alkyl of one to six carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers. $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, and cyclohexyl.

The terms "heterocycle" as used herein by itself or as part of another group refer to non-aromatic, fully saturated or partially unsaturated cyclic groups (for example, 3 to 6 membered monocyclic ring systems) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms. An optionally substituted heterocyclic refers to a heterocyclic having optionally one or more substituents (for example 1 to 4 substituents, or for example 1, 2, 3 or 4), selected from those defined above for substituted alkyl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl; in particular piperidinyl, morpholinyl, and piperazinyl.

The term "halo" or "halogen" as a group or part of a group is generic for fluoro, chloro, bromo, or iodo, as well as any suitable isotope thereof.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic and/or diagnostic agent Where groups may be optionally substituted, such groups may be substituted once or more, and preferably once, twice or thrice. Substituents may be selected from, those defined above for substituted alkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula I and any subgroup thereof. This term also refers to the compounds as provided in Example 1, their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

The present invention further provides compounds of Formula (Ia) or (Ib), or a stereoisomer, tautomer, racemic, metabolite, pro- or predrug, salt, hydrate, N-oxide form, or solvate thereof,

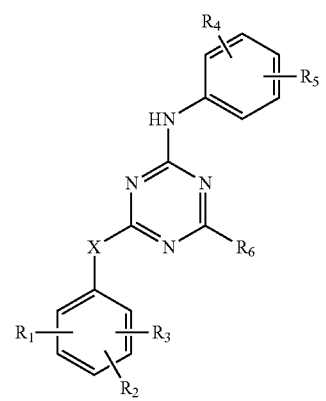

(Ia)

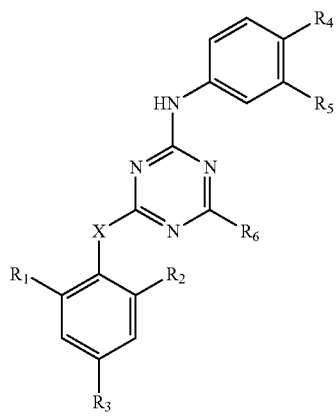

(Ib)

Wherein one or more of the following applies:
$R_1$, $R_2$, and $R_3$ are each independently selected from the list comprising —$C_{1-6}$alkyl, -halo, and —CH=CH—CN;
$R_4$ and $R_5$ are each independently selected from the list comprising —H, —CN, and —CH=CH—CN;
$R_6$ is selected from the list comprising —H, and —NR$_7$R$_8$;
$R_7$ and $R_8$ are each independently selected from the list comprising —H, —$C_{1-6}$alkyl, and -phenyl; said -phenyl being optionally substituted with —CN; or
$R_7$ and $R_8$ taken together with the N atom to which they are attached form a 5- or 6-membered heterocycle comprising from 1 to 3 heteroatoms selected from N, S and O;
X is selected from the list comprising —NH—, —NC$_{1-6}$alkyl-, —O—; and
wherein at least one or $R_1$-$R_5$ is —CH=CH—CN In a particular embodiment, the present invention provides compounds of Formula (Ia) or (Ib), or a stereoisomer, tautomer, racemic, metabolite, pro- or predrug, salt, hydrate, N-oxide form, or solvate thereof,
wherein
$R_1$ and $R_2$ are each independently selected from the list comprising —$C_{1-6}$alkyl, and -halo;
$R_3$ is —CH=CH—CN;
$R_4$ and $R_5$ are each independently selected from the list comprising —H, and —CN;
$R_6$ is selected from the list comprising —H, and —NR$_7$R$_8$;
$R_7$ and $R_8$ are each independently selected from the list comprising —H, —$C_{1-6}$alkyl, and -phenyl; said -phenyl being optionally substituted with —CN; or
$R_7$ and $R_8$ taken together with the N atom to which they are attached form a 5- or 6-membered heterocycle comprising from 1 to 3 heteroatoms selected from N, S and O;
X is selected from the list comprising —NH—, —NC$_{1-6}$alkyl-, —O—.

Exemplary compounds and reaction schemes for synthesis of compounds according to this embodiment are detailed in example 1.

In another particular embodiment, the present invention provides compounds of Formula (Ia) or (Ib), or a stereoisomer, tautomer, racemic, metabolite, pro- or predrug, salt, hydrate, N-oxide form, or solvate thereof,
wherein
$R_1$, $R_2$, and $R_3$ are each independently selected from the list comprising —$C_{1-6}$alkyl, -halo, and —CH=CH—CN;
$R_4$ and $R_5$ are each independently selected from the list comprising —H, and —CN;
$R_6$ is —NR$_7$R$_8$;
$R_7$ and $R_8$ are each independently selected from the list comprising —H, —$C_{1-6}$alkyl, and -phenyl; said -phenyl being optionally substituted with —CN; or
$R_7$ and $R_8$ taken together with the N atom to which they are attached form a 5- or 6-membered heterocycle comprising from 1 to 3 heteroatoms selected from N, S and O;
X is selected from the list comprising —NH—, —NC$_{1-6}$alkyl-, —O—; and
wherein at least one or $R_1$-$R_3$ is —CH=CH—CN In yet another particular embodiment, the present invention provides compounds of Formula (Ia) or (Ib), or a stereoisomer, tautomer, racemic, metabolite, pro- or predrug, salt, hydrate, N-oxide form, or solvate thereof,
wherein
$R_1$ and $R_2$ are each independently selected from the list comprising —$C_{1-6}$alkyl, and -halo;
$R_3$ is —CH=CH—CN;
$R_4$ and $R_5$ are each independently selected from the list comprising —H, —CN, and —CH=CH—CN;
$R_6$ is —NR$_7$R$_8$;
$R_7$ and $R_8$ are each independently selected from the list comprising —H, —$C_{1-6}$alkyl, and -phenyl; said -phenyl being optionally substituted with —CN; or
$R_7$ and $R_8$ taken together with the N atom to which they are attached form a 5- or 6-membered heterocycle comprising from 1 to 3 heteroatoms selected from N, S and O;
X is selected from the list comprising —NH—, —NC$_{1-6}$alkyl-, —O—

In a further particular embodiment, the present invention provides compounds of Formula (Ia) or (Ib), or a stereoisomer, tautomer, racemic, metabolite, pro- or predrug, salt, hydrate, N-oxide form, or solvate thereof,
wherein
$R_1$ and $R_2$ are each independently selected from the list comprising —$C_{1-6}$alkyl, and -halo;
$R_3$ is —CH=CH—CN;
$R_4$ is —CN;
$R_5$ is —H;
$R_6$ is —NR$_7$R$_8$;
$R_7$ and $R_8$ are each independently selected from the list comprising —H and —$C_{1-6}$alkyl;
X is selected from the list comprising —NH— and —O—

In yet a further interesting embodiment, the present invention provides a compound according to Formula (Ia) or (Ib), or a stereoisomer, tautomer, racemic, metabolite, pro- or predrug, salt, hydrate, N-oxide form, or solvate thereof, wherein One or more of $R_1$-$R_5$ is —CH=CH—CN such as:
  $R_1$ is —CH=CH—CN, or $R_2$ is —CH=CH—CN, or $R_3$ is —CH=CH—CN, or $R_4$ is —CH=CH—CN, or $R_5$ is —CH=CH—CN; or
  $R_2$ and $R_3$ are —CH=CH—CN, or $R_3$ and $R_4$ are —CH=CH—CN, or $R_3$ and $R_5$ are —CH=CH—CN The other $R_1$-$R_5$, $R_6$, $R_7$, $R_8$, and X are as defined herein above.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

This invention further provides a pharmaceutical composition comprising a compound according to this invention, suitable for use as a human or veterinary medicine.

Furthermore, this invention provides a compound or composition according to this invention for use as a medicine.

This invention also provides a compound or composition according to this invention for use in the prevention and/or treatment of HIV infections in a subject in need thereof.

In a particular aspect this invention provides the use of a compound or composition according to this invention as a non-nucleoside reverse transcriptase inhibitor.

Finally, this invention provides a method for the prevention and/or treatment of HIV infections; said method comprising administering to a subject in need thereof a compound or composition according to this invention.

METHOD OF TREATMENT

Compounds of formula (Ia) and (Ib) a stereoisomer, tautomer, racemic, metabolite, pro- or predrug, salt, hydrate, N-oxide form, or solvate thereof, are inhibitors of non-nucleoside reverse transcriptase inhibitor and are thus believed to be of potential use in the prevention and/or treatment of HIV infections. The methods of the present invention can be utilized in a variety of settings, including, for example, in selecting the optimal treatment course for a patient, in predicting the likelihood of success when treating an individual patient with a particular treatment regimen, in assessing disease progression, in monitoring treatment efficacy, in determining prognosis for individual patients and in assessing predisposition of an individual to benefit from a particular therapy.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. No. 6,372,778, U.S. Pat. No. 6,369,086, U.S. Pat. No. 6,369,087 and U.S. Pat. No. 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for intravaginal administration, for parenteral administration (such as by intravenous, intramuscular or subcutaneous injection or intravenous infusion), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. No. 6,372,778, U.S. Pat. No. 6,369,086, U.S. Pat. No. 6,369,087 and U.S. Pat. No. 6,372,733, as well as to the standard handbooks, such as the latest edition of Remington's Pharmaceutical Sciences.

Some preferred, but non-limiting examples of such preparations include vaginal gels, vaginal creams, vaginal tablets, vaginal suppositories, vaginal rings, tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. An interesting way of formulating the compounds in combination with a cyclodextrin or a derivative thereof has been described in EP-A-721,331. In particular, the present invention encompasses a pharmaceutical composition comprising an effective amount of a compound according to the invention with a pharmaceutically acceptable cyclodextrin.

In addition, co-solvents such as alcohols may improve the solubility and/or the stability of the compounds. In the preparation of aqueous compositions, addition of salts of the compounds of the invention can be more suitable due to their increased water solubility.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the intravaginal, oral, rectal, ocular, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of Formula or any subgroup thereof that, upon suitable administration, is sufficient to achieve the desired therapeutic or prophylactic effect in the individual to which it is administered. Usually, depending on the condition to be prevented or treated and the route of administration, such an effective amount will usually be between 0.01 to 1000 mg per kilogram body weight day of the patient per day, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art. In preferred embodiments, the compounds and compositions of the invention are used orally or parenterally.

The invention will now be illustrated by means of the following synthetic and biological examples, which do not limit the scope of the invention in any way.

EXAMPLES

Example 1

Specific Examples of Compounds According to the Invention

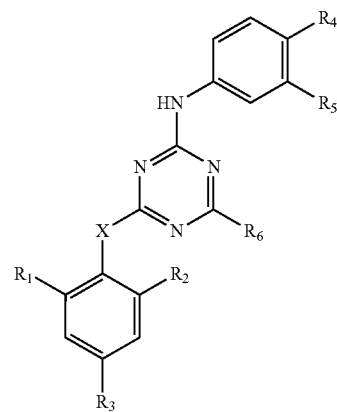

TABLE 1

| Cpd | $R_1$ | $R_2$ | $R_3$ | $R_4$ | $R_5$ | $R_6$ | X |
|---|---|---|---|---|---|---|---|
| T1 | Me | Me | —CH=CH—CN (E/Z) | CN | H | $NH_2$ | NH |
| T2 | Me | Me | —CH=CH—CN (E) | CN | H | $NH_2$ | NH |
| T3 | Me | Me | —CH=CH—CN (Z) | CN | H | $NH_2$ | NH |
| T4 | Me | Me | —CH=CH—CN (E/Z) | CN | H | NHMe | NH |
| T5 | Me | Me | —CH=CH—CN (E/Z) | CN | H | $NMe_2$ | NH |
| T6 | Me | Me | —CH=CH—CN (E/Z) | CN | H | NHiPr | NH |
| T7 | Me | Me | —CH=CH—CN (E/Z) | CN | H | piperidinyl | NH |
| T8 | Me | Me | —CH=CH—CN (E/Z) | CN | H | morpholinyl | NH |
| T9 | Me | Me | —CH=CH—CN (E/Z) | CN | H | N-methylpiperazinyl | NH |
| T10 | F | F | —CH=CH—CN (E/Z) | CN | H | $NH_2$ | NH |
| T11 | Me | Me | —CH=CH—CN (E/Z) | CN | H | $NH_2$ | O |
| T12 | Me | Me | —CH=CH—CN (E/Z) | CN | H | NHMe | O |
| T13 | Me | Me | —CH=CH—CN (E/Z) | CN | H | $NMe_2$ | O |
| T14 | Me | Me | —CH=CH—CN (E/Z) | CN | H | piperidinyl | O |

General Synthetic Schemes for Compounds Belonging to Example 1

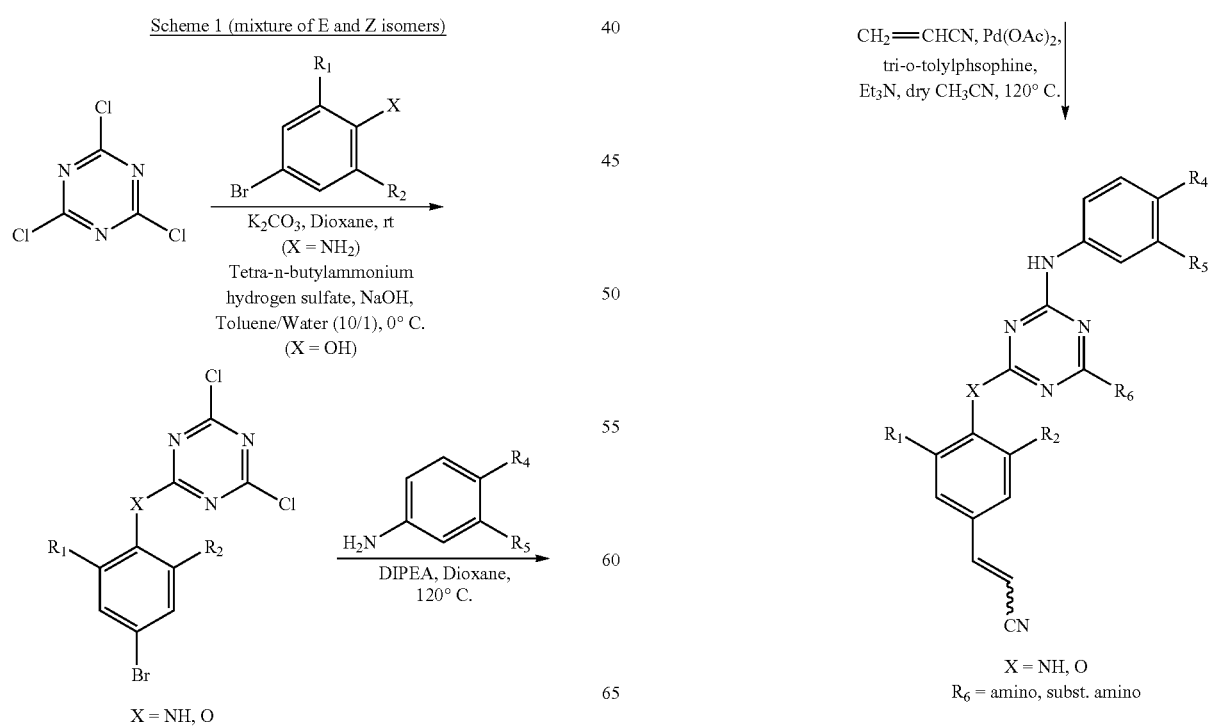

Scheme 2 E isomers

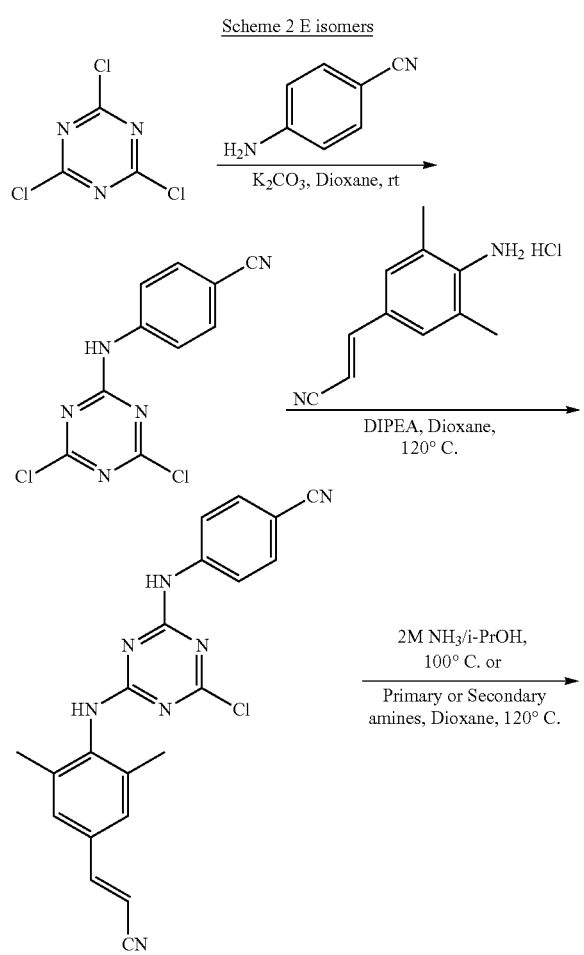

Example 2

Synthesis of Target Compound T1

N-(4-bromo-2,6-dimethylphenyl)-4,6-dichloro-1,3,5-triazin-2-amine (I1)

To a homogenous solution of 2,4,6-trichloro-1,3,5-triazine (3.7 g, 20 mmol) in dioxane (50 mL) was added $K_2CO_3$ (3.1 g, 22 mmol) and 4-bromo-2,6-dimethylaniline (4 g, 20 mmol) and allowed to stir at room temperature for 48 h. Solvents were evaporated and water was added, extracted with EtOAc (3×75 mL), organic layers were washed with $NaHCO_3$, brine and water, dried and evaporated to give dark brown powder (5.5 g, 79%); $^1$H NMR (DMSO-$d_6$, 400 MHz) δ 10.54 (s, 1H), 7.36 (s, 2H), 2.06 (s, 6H); MS (ESI) m/z 349 [M+H]$^+$

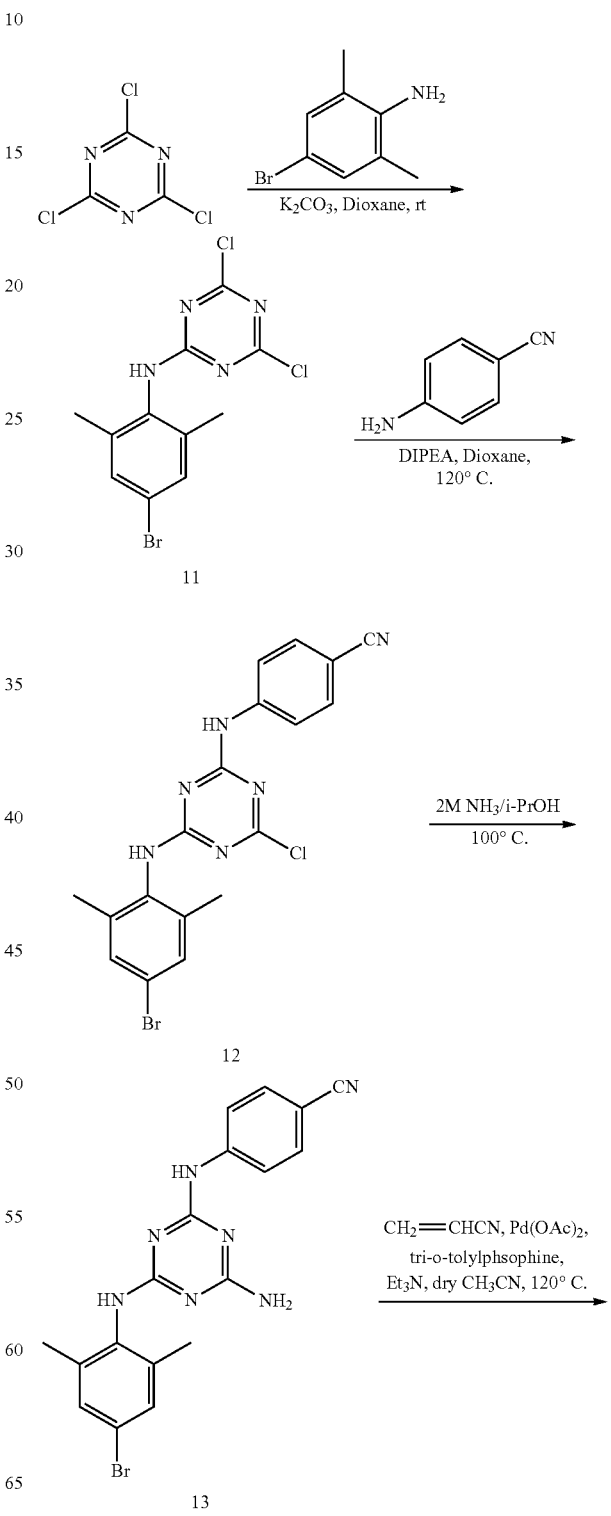

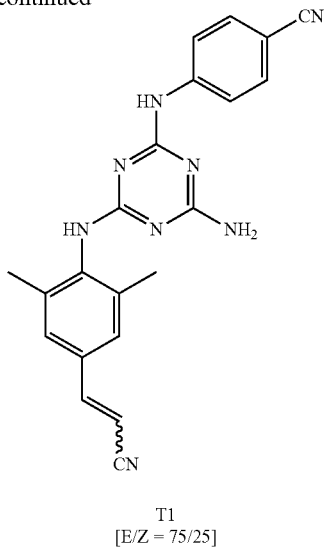

4-((4-((4-bromo-2,6-dimethylphenyl)amino)-6-chloro-1,3,5-triazin-2-yl)amino)benzonitrile (I2)

To a solution of I1 (3.48 g, 10 mmol) in dioxane (25 mL) was added DIPEA (1.75 mL, 10 mmol) and 4-aminobenzonitrile (1.18 g, 10 mmol) and allowed to stir at 120° C. for 24 h. Concentration of the reaction mixture and extraction with EtOAc followed by brine washing afforded dark brown powder. Purification by column chromatography using 30% EtOAc in hexanes afforded light brown powder (2.2 g, 51%); $^1$H NMR (MeOD, 400 MHz) δ 7.72-7.28 (m, 6H), 2.21 (s, 6H); MS (ESI) m/z 431 [M+H]$^+$; LC-MS (214 nm) $t_r$ 19.2 min, 100%

4-((4-amino-6-((4-bromo-2,6-dimethylphenyl)amino)-1,3,5-triazin-2-yl)amino)benzonitrile (I3)

I2 (2.15 g, 5 mmol) was dissolved in 2M NH$_3$/i-PrOH (12.5 mL) in a pressure tube and allowed to stir at 100° C. overnight. Removal of solvent and purification by column chromatography using 60 EtOAc in hexanes afforded white powder (1.5 g, 73%); $^1$H NMR (MeOD, 400 MHz) δ 8.00 (br s, 1H), 7.63 (br s, 2H), 7.42-7.34 (m, 3H), 2.24 (s, 6H); MS (ESI) m/z 411 [M+H]$^+$; LC-MS (214 nm) $t_r$ 17.0 min, 100%

4-(4-amino-6-(4-(2-cyanovinyl)-2,6-dimethylphenylamino)-1,3,5-triazin-2-ylamino)benzonitrile (T1)

A mixture of I3 (0.3 g, 0.75 mmol), acrylonitrile (0.5 mL, 7.5 mmol), Pd(OAc)$_2$ (0.034 g, 0.15 mmol), Et$_3$N (0.2 mL, 1.5 mmol) and tri-o-tolylphosphine (0.23 g, 0.75 mmol) in dry acetonitrile (20 mL) was stirred in a pressure tube at 120° C. overnight. The reaction mixture was filtered and concentrated. Water was added and the mixture was extracted with CH$_2$Cl$_2$. The combined organic layers were dried over Na$_2$SO$_4$ and concentrated. Purification of the residue by column chromatography using 100% EtOAc in hexanes afforded white amorphous powder (0.06 g, 21%). $^1$H NMR (MeOD, 400 MHz) δ 7.96-7.31 (m, 7H), 6.18 and 5.62 [d, J=16.7 Hz (E) and d, J=12.0 Hz (Z), 1H], 2.29 (br s, 6H); MS (ESI) m/z 383 [M+H]$^+$; LC-MS (214 nm) $t_r$ 15.4-15.8 min, 100%

Example 3

Separation of Target Compounds T2 and T3 from T1

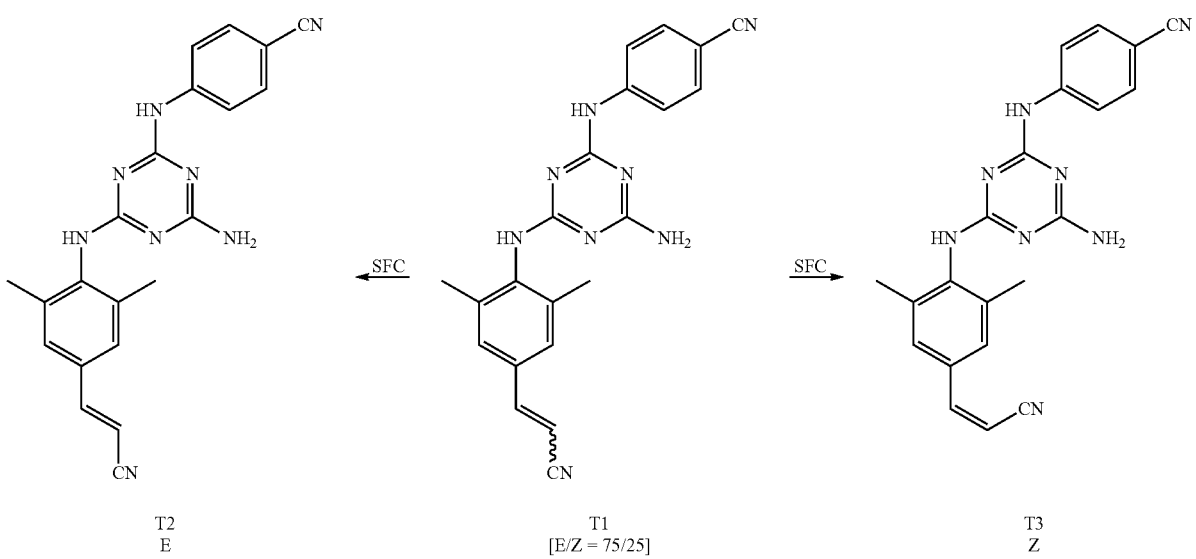 [SMILES: Cc1cc(/C=C/C#N)cc(C)c1Nc1nc(N)nc(Nc2ccc(C#N)cc2)n1 ; "SFC" ; Cc1cc(C=CC#N)cc(C)c1Nc1nc(N)nc(Nc2ccc(C#N)cc2)n1 ; "SFC" ; Cc1cc(/C=C\C#N)cc(C)c1Nc1nc(N)nc(Nc2ccc(C#N)cc2)n1]

T1 is a mixture of E and Z isomers in the ratio 3:1 (E/Z=75/25). Supercritical Fluid Chromatography (SFC) has been used to separate the isomers T2 (E isomer) and T3 (Z isomer) from T1 (mixture of E and Z).

(E)-4-(4-amino-6-(4-(2-cyanovinyl)-2,6-dimethylphenylamino)-1,3,5-triazin-2-ylamino)benzonitrile (T2)

$^1$H NMR (MeOD, 400 MHz) δ 8.0 (br s, 1H), 7.63-7.39 (m, 6H), 6.22 (d, J=16.5 Hz, 1H), 2.30 (s, 6H); MS (ESI) m/z 383 [M+H]$^+$; LC-MS (214 nm) $t_r$ 15.2 min, 99%

(Z)-4-(4-amino-6-(4-(2-cyanovinyl)-2,6-dimethyl-phenylamino)-1,3,5-triazin-2-ylamino)benzonitrile (T3)

$^1$H NMR (MeOD, 400 MHz) δ 8.0 (br s, 1H), 7.64-7.29 (m, 6H), 5.66 (d, J=11.9 Hz, 1H), 2.31 (s, 6H); MS (ESI) m/z 383 [M+H]$^+$; LC-MS (214 nm) t$_r$ 14.8 min, 96%

Example 4

Synthesis of Target Compounds T4-T6

4-((4-((4-bromo-2,6-dimethylphenyl)amino)-6-(methylamino)-1,3,5-triazin-2-yl)amino)benzonitrile (I4)

To a solution of I2 (0.86 g, 2 mmol) in dioxane (25 mL) was added DIPEA (0.68 mL, 4 mmol) and 2M CH$_3$NH$_2$ in dioxane (2 mL, 4 mmol) and allowed to stir at 120° C. for 24 h. Concentration of the reaction mixture and extraction with EtOAc followed by brine washing afforded dark brown powder. Purification by column chromatography using 50% EtOAc in hexanes afforded white powder (0.65 g, 77%); $^1$H NMR (MeOD, 400 MHz) δ 7.65 (br s, 2H), 7.43-7.29 (m, 4H), 3.34 (s, 3H), 2.24 (s, 6H); MS (ESI) m/z 425 [M+H]$^+$ 4-((4-((4-bromo-2,6-dimethylphenyl)amino)-6-(dimethylamino)-1,3,5-triazin-2-yl)amino)benzonitrile (I5)

The above compound was prepared from 2M (CH$_3$)$_2$NH in dioxane and 12 using the procedure similar to I4
Yield: 73%
$^1$H NMR (DMSO-d$_6$, 400 MHz) δ 9.5 (br s, 1H), 8.6 (br s, 1H), 8.0 (br s, 1H), 7.7 (br s, 2H), 7.5 (br s, 2H), 7.4 (br s, 1H), 3.1 (br s, 6H), 2.14 (br s, 6H); MS (ESI) m/z 439 [M+H]$^+$ 4-((4-((4-bromo-2,6-dimethylphenyl)amino)-6-(isopropylamino)-1,3,5-triazin-2-yl)amino)benzonitrile (I6)

The above compound was prepared from propan-2-amine and I2 using the procedure similar to I4
Yield: 64%
$^1$H NMR (MeOD, 400 MHz) δ 7.71 (br s, 2H), 7.49-7.39 (m, 4H), 4.2 (s, 1H), 2.3 (br s, 3H), 1.33 (s, 6H); MS (ESI) m/z 453 [M+H]$^+$

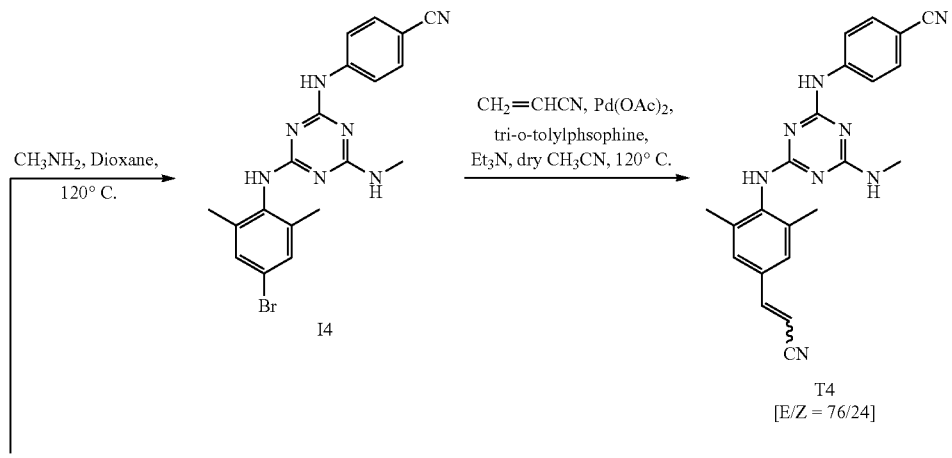

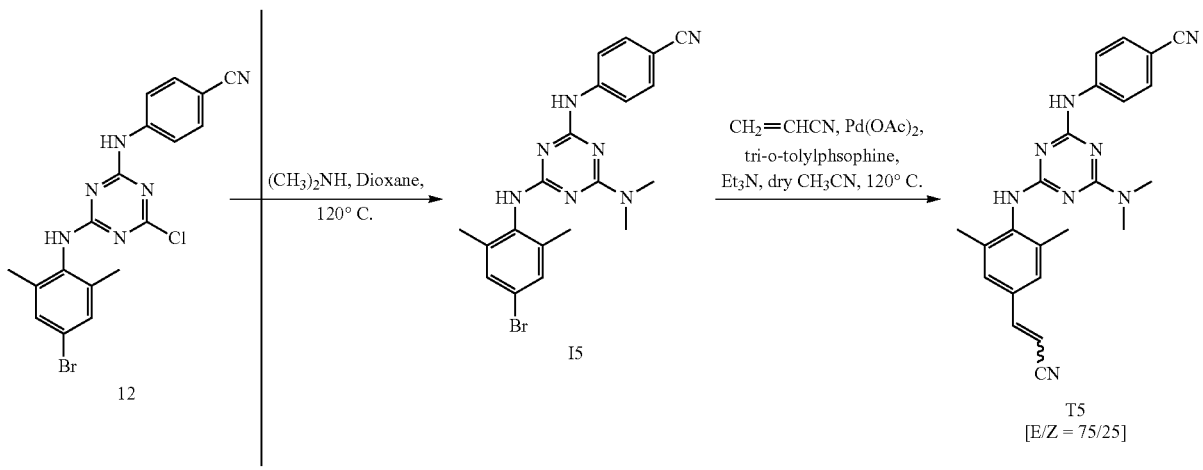

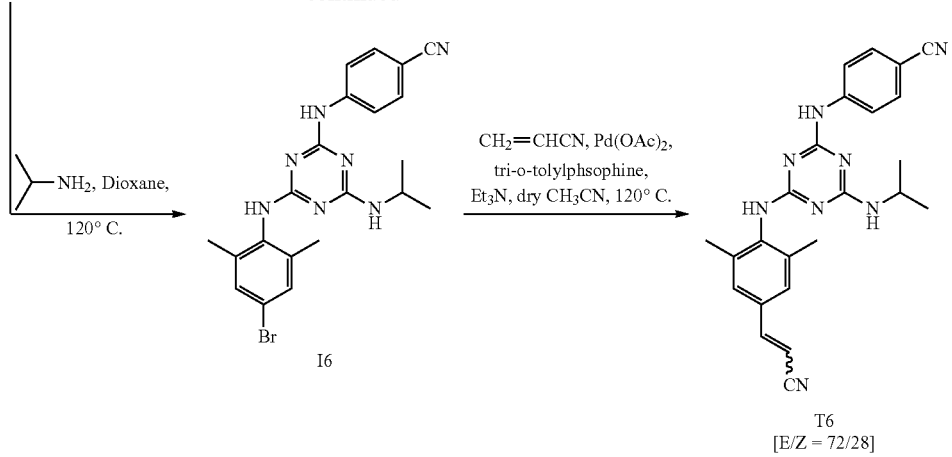

4-((4-((4-(2-cyanovinyl)-2,6-dimethylphenyl)amino)-6-(methylamino)-1,3,5-triazin-2-yl)amino)benzonitrile (T4)

The above compound was prepared from 14 using the procedure similar to T1

Yield: 10%

$^1$H NMR (MeOD, 400 MHz) δ 7.64-7.36 (m, 7H), 6.22 and 5.65 [d, J=16.7 Hz (E) and d, J=11.9 Hz (Z), 1H], 2.86 (br s, 3H), 2.29 (s, 6H); MS (ESI) m/z 397 [M+H]$^+$; LC-MS (214 nm) t$_r$ 16.3 min, 100%

4-((4-((4-(2-cyanovinyl)-2,6-dimethylphenyl)amino)-6-(dimethylamino)-1,3,5-triazin-2-yl)amino)benzonitrile (T5)

The above compound was prepared from I5 using the procedure similar to T1

Yield: 13%

$^1$H NMR (MeOD, 400 MHz) δ 7.44-7.10 (m, 7H), 6.21 and 5.63 [d, J=16.7 Hz (E) and d, J=12.1 Hz (Z), 1H], 3.2 (br s, 6H), 2.29 (s, 6H); MS (ESI) m/z 411[M+H]$^+$; UPLC (214 nm) t$_r$ 4.16 min, 100%

4-((4-((4-(2-cyanovinyl)-2,6-dimethylphenyl)amino)-6-(isopropylamino)-1,3,5-triazin-2-yl)amino)benzonitrile (T6)

The above compound was prepared from I6 using the procedure similar to T1

Yield: 32%

$^1$H NMR (MeOD, 400 MHz) δ 7.60-7.38 (m, 7H), 6.21 and 5.66 [d, J=16.7 Hz (E) and d, J=11.9 Hz (Z), 1H], 4.2 (br s, 1H), 2.24 (s, 6H), 1.25 (br s, 6H); MS (ESI) m/z 425 [M+H]$^+$; LC-MS (214 nm) t$_r$ 17.5 min, 100%

Example 5

Synthesis of Target Compounds T7-T9

4-((4-((4-bromo-2,6-dimethylphenyl)amino)-6-(piperidin-1-yl)-1,3,5-triazin-2-yl)amino)benzonitrile (I7)

The above compound was prepared from piperidine and I2 using the procedure similar to I4

Yield: 42%

MS (ESI) m/z 479 [M+H]$^+$

4-((4-((4-bromo-2,6-dimethylphenyl)amino)-6-morpholino-1,3,5-triazin-2-yl)amino)benzonitrile (I8)

The above compound was prepared from morpholine and I2 using the procedure similar to I4

Yield: 62%

$^1$H NMR (DMSO-d$_6$, 400 MHz) δ 9.60 (br s, 1H), 8.66 (br s, 1H), 7.99 (s, 1H), 7.69 (br s, 2H), 7.50 (br s, 1H), 7.33 (br s, 2H), 3.74-3.57 (m, 8H), 2.14 (s, 6H); MS (ESI) m/z 481 [M+H]$^+$

4-((4-((4-bromo-2,6-dimethylphenyl)amino)-6-(4-methylpiperazin-1-yl)-1,3,5-triazin-2-yl)amino)benzonitrile (I9)

The above compound was prepared from 1-methylpiperazine and I2 using the procedure similar to I4

Yield: 69%

$^1$H NMR (MeOD, 400 MHz) δ 7.9 (br s, 1H), 7.6 (br s, 2H), 7.4-7.2 (m, 3H), 3.9 (br s, 4H), 2.5 (br s, 4H), 2.3 (br s, 3H), 2.2 (s, 6H); MS (ESI) m/z 493 [M–H]$^-$

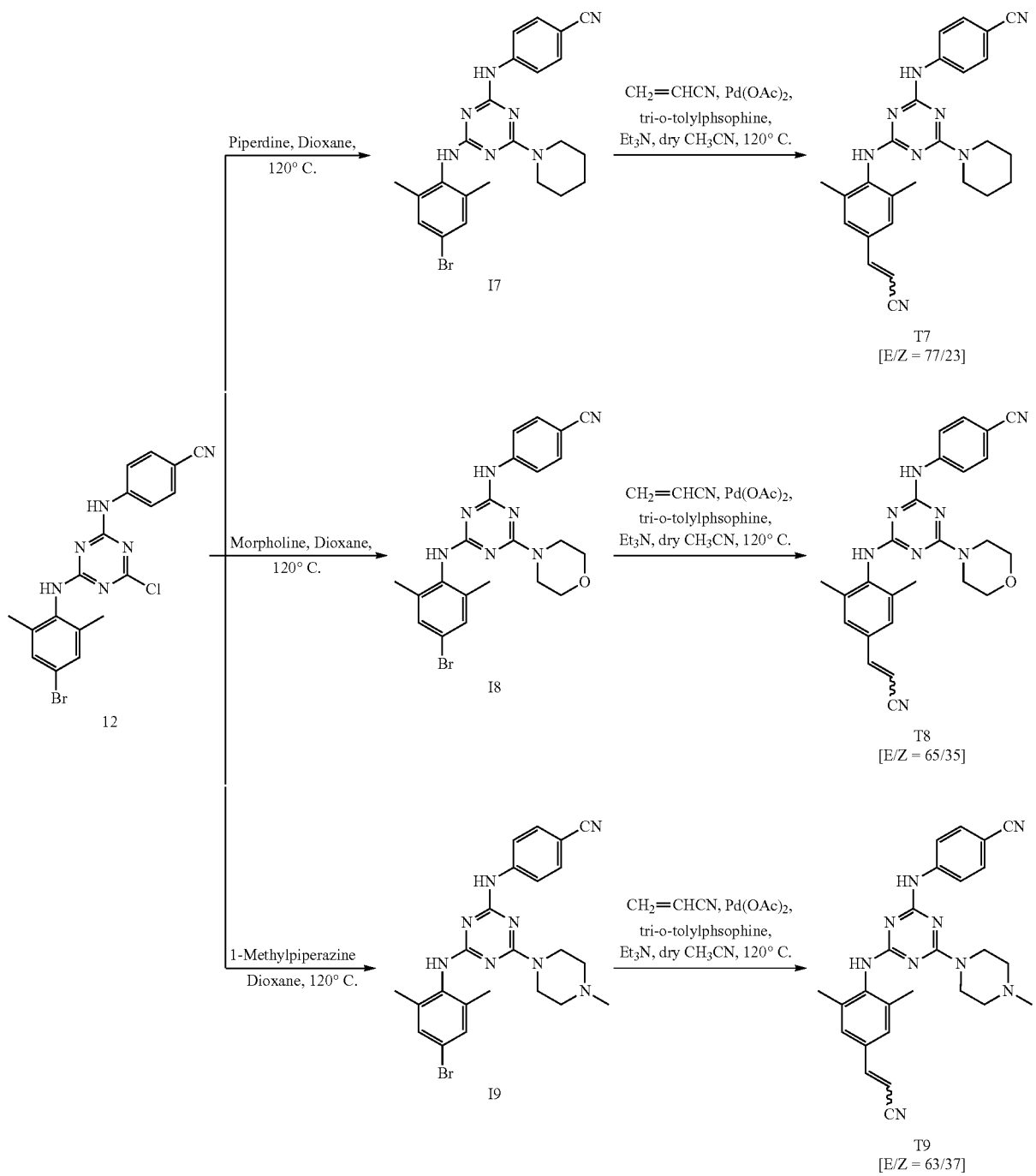

4-((4-((4-(2-cyanovinyl)-2,6-dimethylphenyl)amino)-6-(piperidin-1-yl)-1,3,5-triazin-2-yl)amino)benzonitrile (T7)

The above compound was prepared from I7 using the procedure similar to T1

Yield: 12%

¹H NMR (MeOD, 400 MHz) δ 7.62-7.36 (m, 6H), 6.19 and 5.6 [br s (E) and br s (Z), 1H], 3.83 (br s, 4H), 2.23 (br s, 6H), 1.6 (br s, 6H); MS (ESI) m/z 451[M+H]⁺; LC-MS (214 nm) t$_r$ 19.4 min, 89%

4-((4-((4-(2-cyanovinyl)-2,6-dimethylphenyl)amino)-6-morpholino-1,3,5-triazin-2-yl)amino)benzonitrile (T8)

The above compound was prepared from 18 using the procedure similar to T1

Yield: 20%

¹H NMR (MeOD, 400 MHz) δ 7.72-7.41 (m, 7H), 6.34 and 5.62 [(br s (E) and br s (Z), 1H], 3.86-3.5 (m, 8H), 2.26 (s, 6H); MS (ESI) m/z 453 [M+H]⁺; LC-MS (214 nm) t$_r$ 18.1 min, 91%

4-((4-((4-(2-cyanovinyl)-2,6-dimethylphenyl)amino)-6-(4-methylpiperazin-1-yl)-1,3,5-triazin-2-yl)amino)benzonitrile (T9)

The above compound was prepared from I9 using the procedure similar to T1

Yield: 23%

$^1$H NMR (MeOD, 400 MHz) δ 7.75-7.39 (m, 7H), 6.25 and 5.6 [br s (E) and br s (Z), 1H], 3.92 (br s, 4H), 2.56 (br s, 4H), 2.39 (br s, 3H), 2.29 (s, 6H); MS (ESI) m/z 466 [M+H]$^+$; LC-MS (214 nm) t$_r$ 13.8 min, 100%

Example 6

Synthesis of Target Compound T10

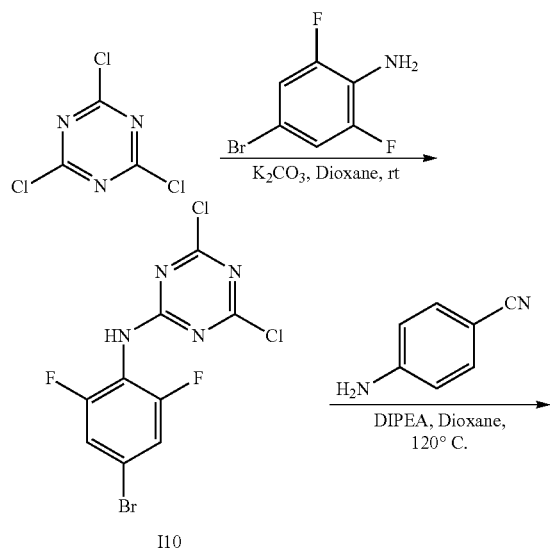

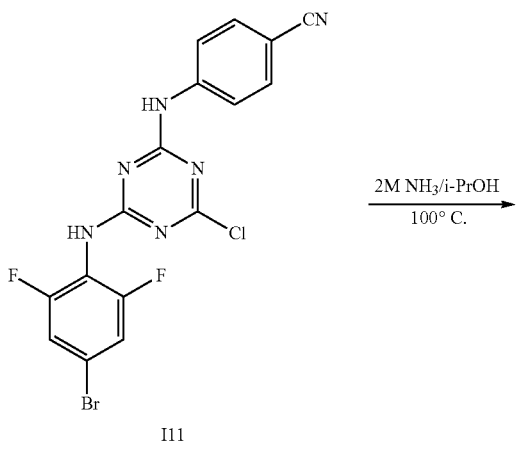

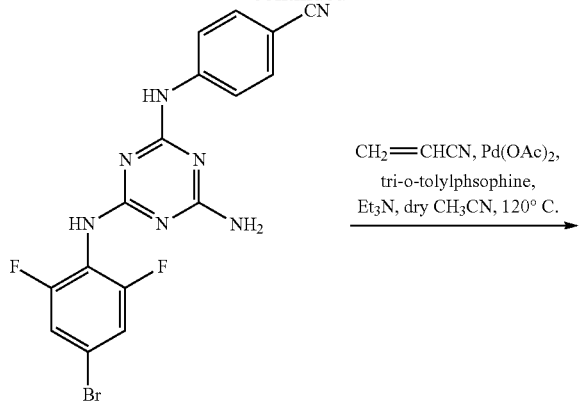

N-(4-bromo-2,6-difluorophenyl)-4,6-dichloro-1,3,5-triazin-2-amine (I10)

The above compound was prepared from 4-bromo-2,6-difluoroaniline using the procedure similar to I1

Yield: 84%

MS (ESI) m/z 357 [M+H]$^+$

4-((4-((4-bromo-2,6-difluorophenyl)amino)-6-chloro-1,3,5-triazin-2-yl)amino)benzonitrile (I11)

The above compound was prepared from I10 using the procedure similar to I2

Yield: 46%

$^1$H NMR (DMSO-d$_6$, 400 MHz) δ 10.75 (s, 1H), 10.25 (s, 1H), 8.01-7.63 (m, 6H); MS (ESI) m/z 438 [M+H]$^+$

4-((4-amino-6-((4-bromo-2,6-difluorophenyl)amino)-1,3,5-triazin-2-yl)amino)benzonitrile (I12)

The above compound was prepared from I11 using the procedure similar to I3

Yield: 88%

$^1$H NMR (DMSO-d$_6$, 400 MHz) δ 9.58 (s, 1H), 7.89 (br s, 1H), 7.58 (br s, 3H), 7.31 (br s, 3H), 6.78 (s, 2H); MS (ESI) m/z 419 [M+H]$^+$ 4-((4-amino-6-((4-(2-cyanovinyl)-2,6-difluorophe-nyl)amino)-1,3,5-triazin-2-yl)amino)benzonitrile (T10)

The above compound was prepared from I12 using the procedure similar to T1

Yield: 17%

$^1$H NMR (MeOD, 400 MHz) δ 7.83 (d, J=8.3 Hz, 2H), 7.59-7.54 (m, 4H), 7.40-7.32 (m, 1H), 6.36 and 5.84 [d, J=16.6 Hz (E) and d, J=12.1 Hz (Z), 1H]; MS (ESI) m/z 391 [M+H]$^+$; LC-MS (214 nm) t$_r$ 15.1 min, 100%

Example 7

Synthesis of Target Compound T11

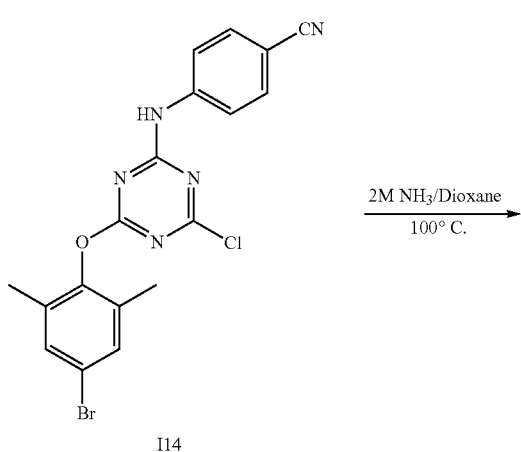

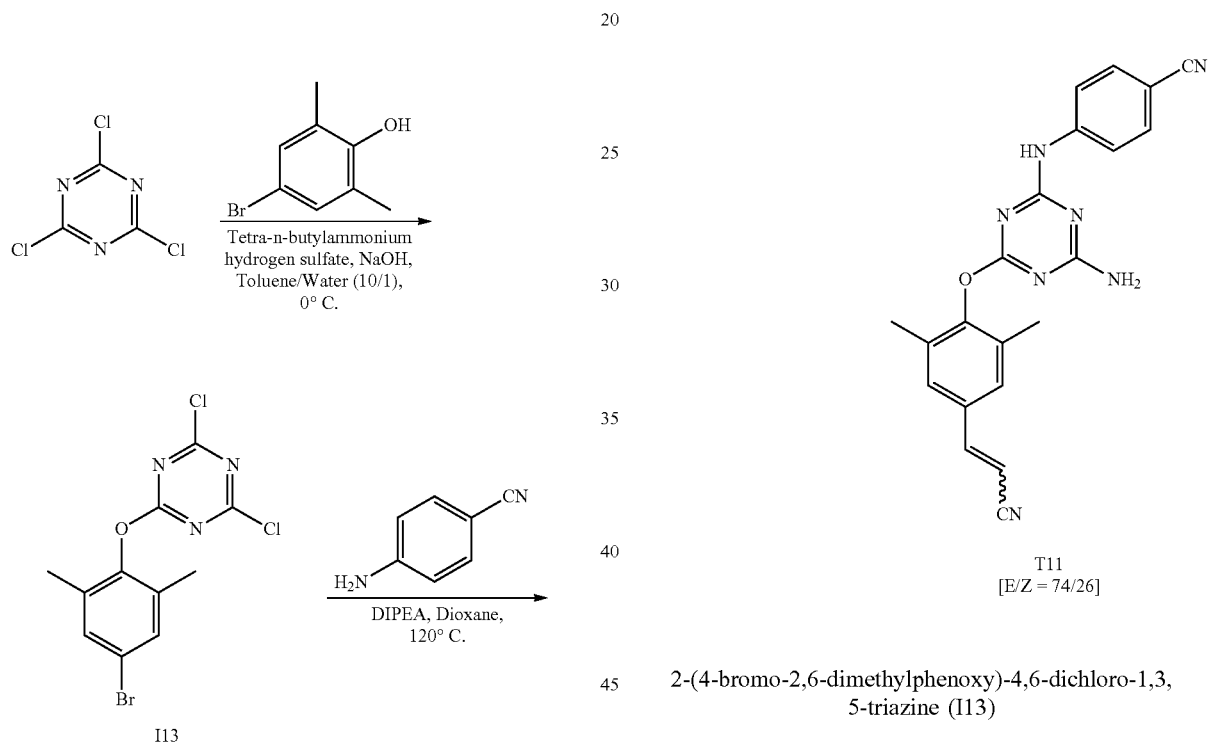

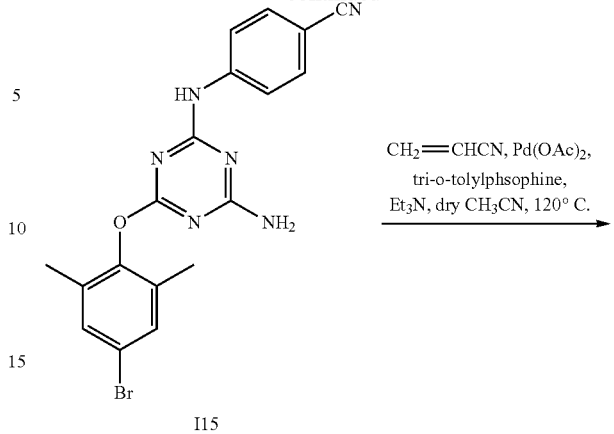

2-(4-bromo-2,6-dimethylphenoxy)-4,6-dichloro-1,3,5-triazine (I13)

To a solution of 2,4,6-trichloro-1,3,5-triazine (5.53 g, 30 mmol) and 2,4,6-trimethylphenol (6.03 g, 30 mmol) and tetra-n-butyl ammonium hydrogen sulfate (0.1 g, 0.30 mmol) in 100 mL of toluene at 0° C. was added slowly 10 mL of NaOH (1.2 g, 30 mmol) and allowed to stir at 0° C. for 2 h and then at room temperature for 36 h. EtOAc was added and washed with water, 10% HCl and brine. Removal of solvent afforded white powder (8.4 g, 80%)

$^1$H NMR (DMSO-d$_6$, 400 MHz) δ 7.36 (s, 2H), 2.11 (s, 6H); MS (ESI) m/z 350 [M+H]$^+$ 4-((4-(4-bromo-2,6-dimethylphenoxy)-6-chloro-1,3,5-triazin-2-yl)amino)benzonitrile (I14)

The above compound was prepared from I13 using the procedure similar to I2

Yield: 65%

$^1$H NMR (MeOD, 400 MHz) δ 8.00-7.45 (m, 6H), 2.10 (br s, 6H); MS (ESI) m/z 432 [M+H]$^+$; LC-MS (214 nm) t$_r$ 19.8 min, 100%

4-((4-amino-6-(4-bromo-2,6-dimethylphenoxy)-1,3,5-triazin-2-yl)amino)benzonitrile (I15)

The above compound was prepared from I14 using the procedure similar to I3.
Yield: 63%
$^1$H NMR (DMSO-d6, 400 MHz) δ 7.85 (br s, 2H), 7.61 (s, 2H), 7.37 (br s, 4H), 2.10 (br s, 6H); MS (ESI) m/z 412 [M+H]$^+$; LC-MS (214 nm) t$_r$ 18.3 min, 100%

4-((4-amino-6-(4-(2-cyanovinyl)-2,6-dimethylphenoxy)-1,3,5-triazin-2-yl)amino)benzonitrile (T11)

The above compound was prepared from I15 using the procedure similar to T1
Yield: 39%
$^1$H NMR (MeOD, 400 MHz) δδ 8.0 (br s, 1H), 7.65 (m, 4H), 7.40 (br s, 2H), 6.23 and 5.67 [d, J=16.7 Hz and d, J=12.1 Hz, 1H], 2.2 (br s, 6H); MS (ESI) m/z 384 [M+H]$^+$; LC-MS (214 nm) t$_r$ 16.7 min, 100%

Example 8

Synthesis of target compounds T12-T14

4-((4-(4-bromo-2,6-dimethylphenoxy)-6-(methylamino)-1,3,5-triazin-2-yl)amino)benzonitrile (I16)

The above compound was prepared from 2M CH$_3$NH$_2$ in dioxane and I14 using the procedure similar to I4
Yield: 58%
MS (ESI) m/z 426 [M+H]$^+$ 4-((4-(4-bromo-2,6-dimethylphenoxy)-6-(dimethylamino)-1,3,5-triazin-2-yl)amino)benzonitrile (I17)

The above compound was prepared from 2M (CH$_3$)$_2$NH in dioxane and I14 using the procedure similar to I4
Yield: 59%
$^1$H NMR (DMSO-d6, 400 MHz) δ 10.1 (s, 1H), 7.78-7.63 (m, 4H), 7.38 (s, 2H), 3.15 (s, 3H), 3.03 (s, 3H), 2.17 (s, 6H); MS (ESI) m/z 440 [M+H]$^+$

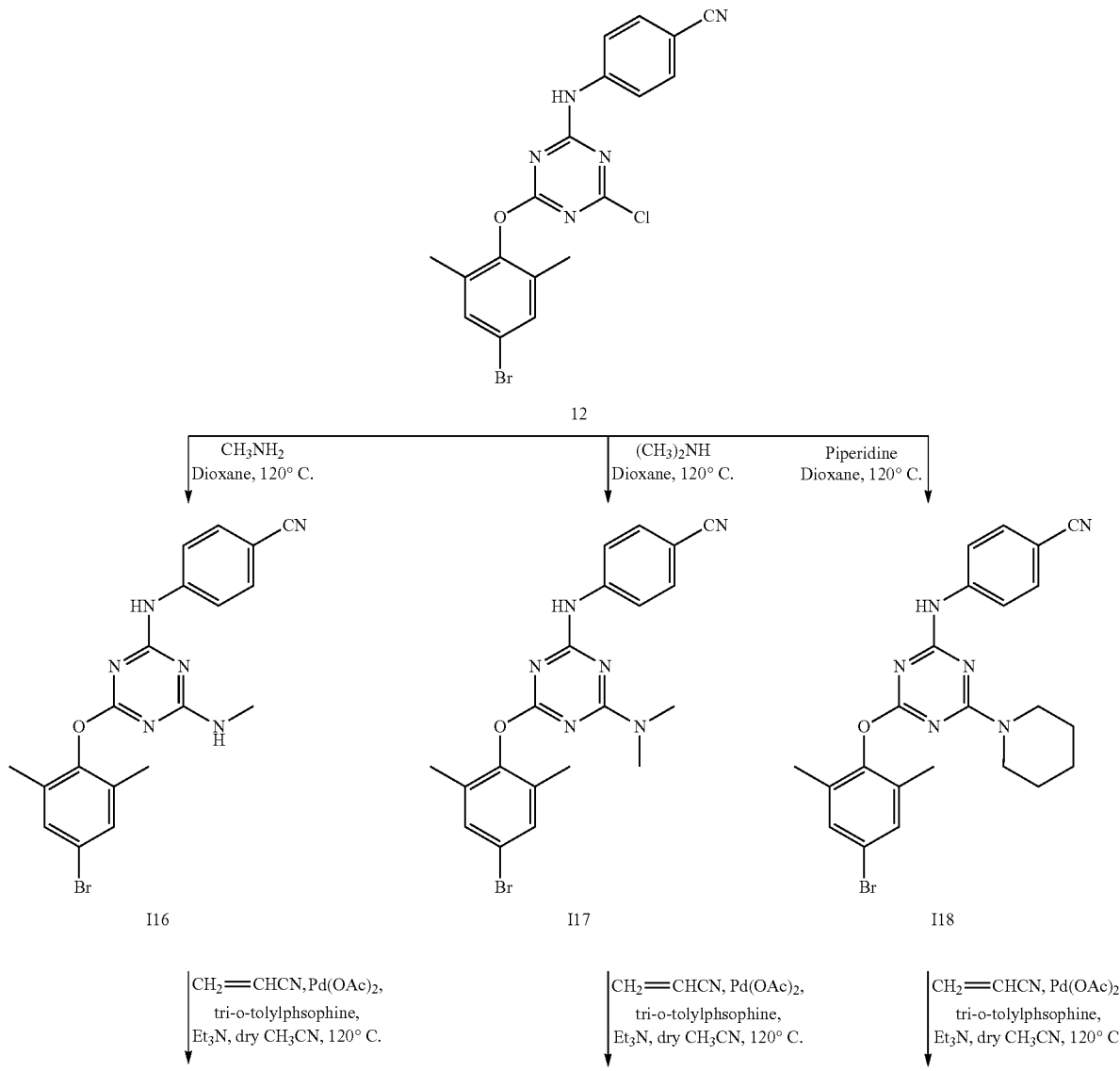

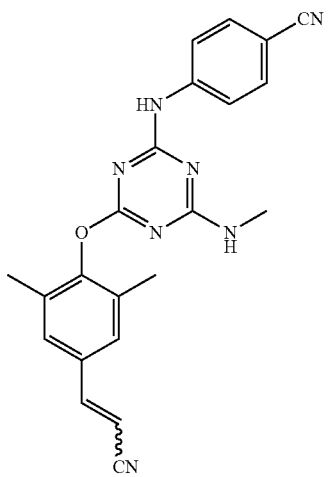
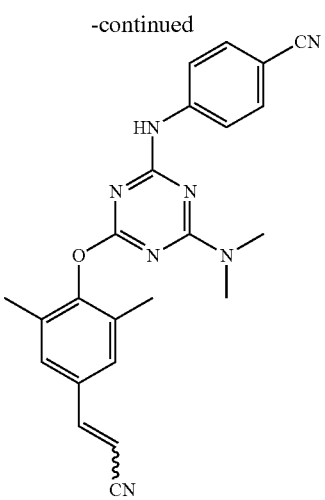
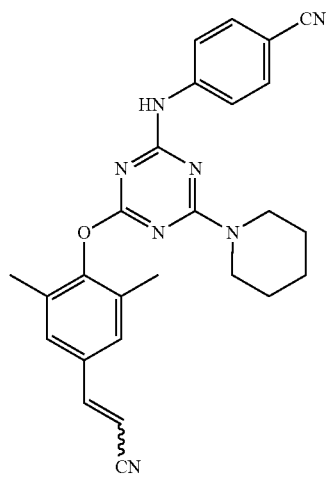

T12 (E/Z = 77/23)   T13 (E/Z = 72/28)   T14 (E/Z = 75/25)

4-((4-(4-bromo-2,6-dimethylphenoxy)-6-(piperidin-1-yl)-1,3,5-triazin-2-yl)amino)benzonitrile (I18)

The above compound was prepared from piperidine and I14 using the procedure similar to I4
Yield: 35%
$^1$H NMR (DMSO-d6, 400 MHz) δ 10.1 (s, 1H), 7.74-7.60 (m, 4H), 7.43 (s, 2H), 3.80 (br s, 2H), 3.66 (br s, 2H), 2.17 (s, 6H), 1.65-1.53 (m, 6H); MS (ESI) m/z 480 [M+H]$^+$ 4-((4-(4-(2-cyanovinyl)-2,6-dimethylphenoxy)-6-(methylamino)-1,3,5-triazin-2-yl)amino)benzonitrile (T12)

The above compound was prepared from I16 using the procedure similar to T1
Yield: 23%
$^1$H NMR (MeOD, 400 MHz) δ 7.73-7.30 (m, 7H), 6.21 and 5.66 (d, J=16.7 Hz (E) and d, J=12.1 Hz (Z), 1H), 2.99 (br s, 3H), 2.19 (s, 6H); MS (ESI) m/z 398 [M+H]$^+$; LC-MS (214 nm) $t_r$ 17.8 min, 100%

4-((4-(4-(2-cyanovinyl)-2,6-dimethylphenoxy)-6-(dimethylamino)-1,3,5-triazin-2-yl)amino)benzonitrile (T13)

The above compound was prepared from I17 using the procedure similar to T1
Yield: 32%
$^1$H NMR (MeOD, 400 MHz) δ 7.73-7.30 (m, 7H), 6.23 and 5.67 (d, J=16.7 Hz (E) and d, J=12.1 Hz (Z), 1H), 3.25 (br s, 3H), 3.15 (br s, 3H), 2.20 (s, 6H); MS (ESI) m/z 412 [M+H]$^+$; LC-MS (214 nm) $t_r$ 19.1 min, 100%

4-((4-(4-(2-cyanovinyl)-2,6-dimethylphenoxy)-6-(piperidin-1-yl)-1,3,5-triazin-2-yl)amino)benzonitrile (T14)

The above compound was prepared from I18 using the procedure similar to T1
Yield: 27%
$^1$H NMR (MeOD, 400 MHz) δ 7.67-7.40 (m, 7H), 6.21 and 5.67 (d, J=16.7 Hz (E) and d, J=12.1 Hz (Z), 1H), 3.86-3.72 (m, 4H), 2.20 (s, 6H), 1.73-1.62 (m, 6H); MS (ESI) m/z 452 [M+H]$^+$; LC-MS (214 nm) $t_r$ 20.3 min, 100%

Example 9

Alternate Synthesis of Target Compound T2

In Example 3 we reported the separation of T2 (E isomer) from T1 (mixture of E and Z).

We optimized the synthetic scheme to get the compound T2. In this scheme we used starting material (E)-3-(4-amino-3,5-dimethylphenyl)acrylonitrile hydrochloride to synthesize the E isomer T2.

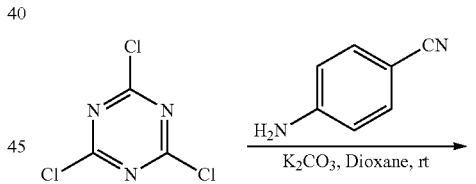

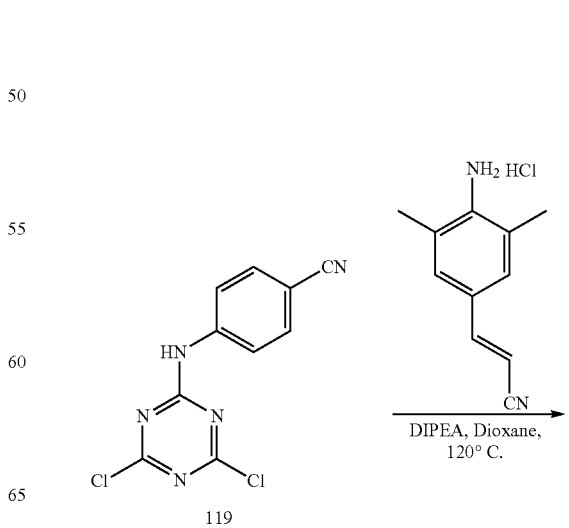

119

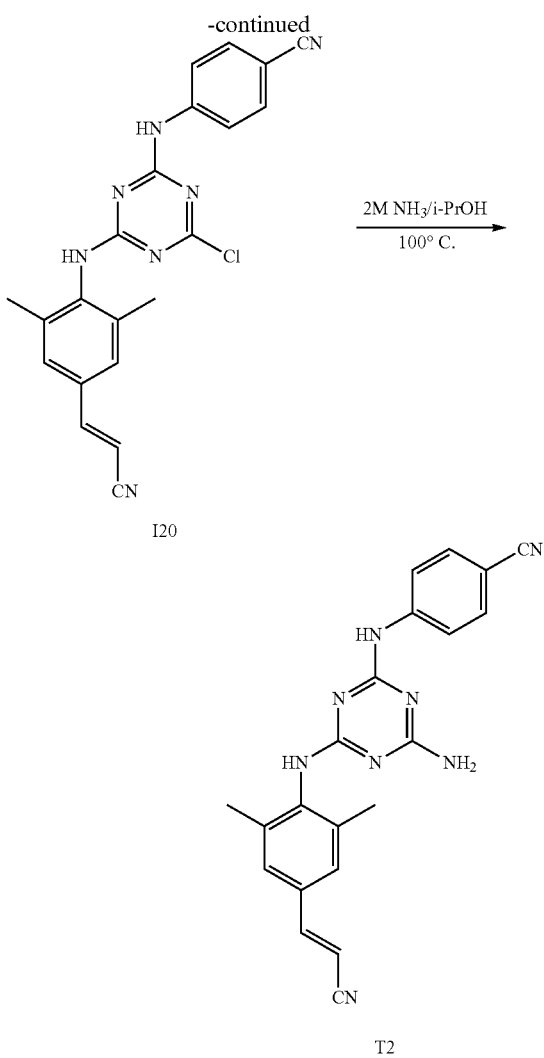

4-((4,6-dichloro-1,3,5-triazin-2-yl)amino)benzonitrile (I19)

To a solution of 2,4,6-trichloro-1,3,5-triazine (1.84 g, 10 mmol) and K₂CO₃ (1.52 g, 11 mmol) in dioxane (50 mL) at 0° C. was added slowly 4-cyanoaniline (1.18 g, 10 mmol) in 50 mL of dioxane and allowed to stir at 0° C. for 2 h and then at room temperature for 36 h. Solvents were evaporated and water was added. The precipitated material was filtered, washed with water and DCM to get light brown powder (1.8 g, 68%); ¹H NMR (DMSO-d₆, 400 MHz) δ 11.5 (s, 1H), 7.88 (d, J=6.8 Hz, 2H), 7.83 (d, J=6.8 Hz, 2H); MS (ESI) m/z 267 [M+H]⁺

(E)-4-((4-chloro-6-((4-(2-cyanovinyl)-2,6-dimethylphenyl)amino)-1,3,5-triazin-2-yl)amino)benzonitrile (I20)

To a solution of I19 (0.53 g, 2 mmol) in dioxane (50 mL) was added DIPEA (0.77 mL, 4.4 mmol) and (E)-3-(4-amino-3,5-dimethylphenyl)acrylonitrile hydrochloride (0.42 g, 2 mmol) and allowed to stir at 120° C. for 24 h. Concentration of the reaction mixture and extraction with EtOAc followed by brine washing afforded dark brown powder (0.8 g, yield quantitative). This powder was used directly in next step without further purification.

(E)-4-(4-amino-6-(4-(2-cyanovinyl)-2,6-dimethylphenylamino)-1,3,5-triazin-2-ylamino)benzonitrile (T2)

I20 (0.8 g, 5 mmol) was dissolved in 2M NH₃/i-PrOH (10 mL) in a pressure tube and allowed to stir at 100° C. overnight. Removal of solvent and purification by column chromatography using 90 EtOAc in hexanes afforded white powder (0.44 g, 58%); ¹H NMR (MeOD, 400 MHz) δ 8.0 (br s, 1H), 7.63-7.36 (m, 6H), 6.22 (d, J=16.5 Hz, 1H), 2.29 (s, 6H); MS (ESI) m/z 383 [M+H]⁺; LC-MS (214 nm) $t_r$ 15.4 min, 100%

Antiviral Assay

Cells

The JC53-BL cell line, also known as the TZM-bl cell line (NIH AIDS Research and Reference Reagent Program, Germantown, USA), was used for the evaluation of anti-HIV activity. TZM-bl cells were cultured in Dulbecco's Minimum Essential Medium (DMEM) (Lonza) containing 10% heat-inactivated FBS and 50 µg gentamycin/mL at 37° C. in a humidified 5% CO₂, 95% air environment. Twice a week the cells were treated with 0.25% trypsin-1 mM EDTA (Lonza) for 10 minutes. The resulting cell suspension was washed with an equivalent amount of TZM-bl medium and subsequently seeded in a T75 culture flask (Greiner Bio-One, Germany) at 10⁶ cells in 20 mL medium.

TZM-bl Assay

The antiviral activity of the newly designed compounds was measured by pre-incubating ten thousand TZM-bl cells (at 10⁵ cells/mL in culture medium supplemented with 30 µg/mL DEAE dextran) in a 96-well plate for 30 minutes at 37° C., 5% CO₂ in the presence or absence of serial dilutions of the respective compound. Subsequently, 200 TCID₅₀ of HIV-1 BaL was added to each well and cultures were incubated for 48 hours before quantifying luciferase activity, using a TriStar LB941 luminometer (Berthold Technologies GmbH & Co. KG, Bad Wildbad, Germany). Each condition was evaluated in triplicate wells and in at least two independent experiments. The antiviral activity of the compound was expressed as the percentage of viral inhibition compared to the untreated controls and subsequently plotted against the compound concentration. Non-linear regression analysis was used to calculate the 50% effective concentration (EC₅₀) based on at least two independent measurements and using GraphPad Prism version 5.03 for Windows (GraphPad Software, San Diego, Calif., USA).

WST-1 Cytotoxicity Assay

The Water Soluble Tetrazolium-1 (WST-1) Cell Proliferation Assay is a colorimetric assay for the measurement of cell proliferation and viability. The assay is based on the cleavage of the tetrazolium salt WST-1 (4-[3-(4-iodophenyl)-2-(4-nitrophenyl)-2H-5-tetrazolio]-1,3-benzene disulfonate) to a formazan dye by a complex cellular mechanism. This bioreduction is largely dependent on the glycolytic production of NAD(P)H in viable cells. Therefore, the amount of formazan dye formed correlates directly to the number of viable cells in the culture, and can be quantified by measuring the absorbance at 450 nm in a multiwell plate reader. The greater the number of viable cells, the greater the amount of formazan dye produced following the addition of WST-1. Cytotoxicity of each compound was evaluated using this WST-1 viability assay, according to the manufacturer's instructions (Roche, Vilvoorde, Belgium).

Briefly, ten thousand TZM-bl cells were seeded in a 96-well plate and cultured for 2 days in the presence of a serial dilution of compound. After this 48 h exposure, Cell Proliferation Reagent, WST-1, was added and absorbance at 450 nm was quantified after 90 min using a microplate reader (BioRad, Tokio, Japan). Each compound was tested in three replicate wells and in at least two independent experiments. The percentage cell viability, compared to untreated controls, was plotted against the compound concentration and non-linear regression analysis was performed using GraphPad Prism version 5.02 for Windows (GraphPad Software, San Diego, Calif., USA) to calculate the 50% cytotoxic concentration ($CC_{50}$).

Anti-HIV-1 Activity

The target compounds are evaluated for their anti-HIV-1 activity and cytotoxicity. In a primary screen, the anti-HIV activity against the laboratory strain Ba-L and against a primary subtype C isolate was determined in the TZM-bl cell line. Cellular toxicity on TZM-bl cells was evaluated using WST-1. Based on the primary screening results, the target compound was further evaluated for anti-HIV activity in different primary cells, including peripheral blood mononuclear cells, dendritic cells and CD4+ T lymphocytes. In addition, the activity against NNRTI-resistant viruses (V106A, Y181C, L100I+K103N, L100I+E138K+T369I and K101E+K103N+V108VI+V179M+Y181C+E138Q) was tested. Diarylpyrimidines (DAPY) TMC120, TMC125 and TMC278 were used as reference compounds.

Table 2 shows the comparison of antiviral activity (wild and resistant viruses) and cytotoxicity of target compounds T1-T14 with TMC120, TMC125, TMC278 and DATA.

TMC120 is now in phase III trial to test the long-term safety and effectiveness for prevention of HIV in african women. TMC120 shows high nanomolar activity against Efavirenz resistant viruses (L100I+K103N) and no activity against NNRTI-resistant viruses (L100I+E138K+T369I and K101E+K103N+V108VI+V179M+Y181C+E138Q). In addition TMC120 is also cytotoxic below 5 μM ($CC_{50}$=2.88 μM). TMC125 (Etravirine) and TMC278 (Rilpivirine) which are currently used in treatment of HIV infections are also cytotoxic below 10 μM.

Replacement of pyrimidine scaffold (TMC120) by triazine (DATA) decreased the cytotoxicity (15 fold) but no improved activity against Efavirenz resistant viruses. Introduction of spacer (for example T2 vs DATA) increases the activity against NNRTI-resistant viruses of HIV-1 to the low nM level. Several target compounds have better profile (improved activity against NNRTI-resistant viruses and also improved cytotoxicity profile) than TMC120.

TABLE 2

Comparison of antiviral activity and cytotoxicity of target compounds T1-T14 with TMC120, TMC125, TMC278 and DATA

| | Antiviral activity-wild type viruses $EC_{50}$ (nM) | | | Antiviral activity-NNRTI-resistant viruses $EC_{50}$ (nM) | | | | | | | | | | Cytotoxicity $CC_{50}$ (μM) |
|---|---|---|---|---|---|---|---|---|---|---|---|---|---|---|
| | TZM-bI | PBMC | DC/T4 | Ba-L | | | | VI829 | | | | | | |
| | | | | | | | | | | L100I+ | | Ba-L | VI829 | |
| Cpd | Ba-L | VI829 | Ba-L | Ba-L | V106A | FC | Y181C | FC | K103N | FC | * | FC | ** | FC | TZM-bI |
| TMC120 | 2.0 | 2.0 | 5.1 | 1.6 | 2.5 | 1 | 10.8 | 5 | 673.5 | 337 | >1000 | >500 | >1000 | >500 | 2.88 |
| TMC125 | 1.5 | 1.5 | 5.9 | 1.8 | 1.6 | 1 | 7.6 | 5 | 14.0 | 9 | 76 | 51 | 93 | 62 | 4.77 |
| TMC278 | 0.72 | 1.0 | 5.2 | 1.6 | 0.93 | 1 | 2.5 | 3 | 3.6 | 4 | 27 | 38 | 130 | 130 | 7.74 |
| DATA | 4.0 | 2.9 | 4.7 | 1.9 | 21.6 | 10 | 33.1 | 15 | 1706.9 | 589 | | | | | 44 |
| T1 | 1.3 | 1.1 | 1.8 | 0.7 | 1.7 | 1 | 4.0 | 3 | 15.0 | 10 | 22.8 | 18 | 232 | 210 | 34.65 |
| T2 | 1.3 | 1.3 | 5.3 | 0.51 | 1.9 | 1 | 2.6 | 2 | 6.8 | 5.2 | 23 | 18 | 89 | 68 | 24.54 |
| T3 | 1.1 | 1.1 | 6.1 | 0.31 | 5.2 | 5 | 12.0 | 11 | 123.0 | 112 | 236 | 214 | 1393 | 1266 | 30.83 |
| T4 | 1.7 | | | | | | | | | | 66 | 39 | | | 5.91 |
| T5 | 5.8 | 4.4 | | | 12.0 | 2 | 27.0 | 6 | 74.0 | 17 | 455 | 78 | 137 | 31 | 8.06 |
| T6 | 5.0 | 4.3 | 14 | 1.4 | 30.0 | 6 | 45.0 | 10 | 184 | 43 | 424 | 85 | 968 | 225 | 24.69 |
| T7 | 18 | 19 | | | 126 | 7 | 221 | 12 | >1000 | >50 | >1000 | >55 | >1000 | >50 | >100 |
| T8 | 7.1 | | | | | | | | | | 634 | 89 | | | 11.40 |
| T9 | 8.5 | | | | | | | | | | 316 | 37 | | | 21.24 |
| T10 | 0.53 | | | | | | | | | | 590 | 1113 | | | 21.41 |
| T11 | 1.1 | 0.64 | | | 2.5 | 2 | 4.1 | 6 | 17.0 | 27 | 62.0 | 56 | 107 | 167 | 19.13 |
| T12 | 1.6 | 1.6 | | | 6.5 | 4 | 7.4 | 5 | 24.0 | 15 | 77.0 | 48 | 70 | 44 | 20.04 |
| T13 | 3.4 | | | | | | | | | | 786 | 231 | | | 7.85 |
| T14 | 21 | | | | | | | | | | >1000 | >47 | | | >100 |

\* = K101E + K103N + V108VI + V179M + Y181C + E138Q
\*\* = L100I + E138K + T369I

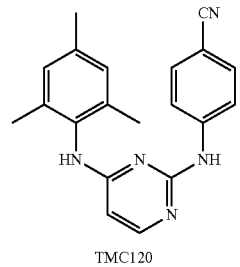 [SMILES: Cc1cc(C)c(Nc2ccnc(Nc3ccc(C#N)cc3)n2)c(C)c1]

TMC120

TABLE 2-continued

Comparison of antiviral activity and cytotoxicity of target compounds T1-T14 with TMC120, TMC125, TMC278 and DATA

| | Antiviral activity-wild type viruses EC$_{50}$ (nM) | | | | | | | | Antiviral activity-NNRTI-resistant viruses EC$_{50}$ (nM) VI829 | | | | | | Cytotoxicity CC$_{50}$ (μM) |
|---|---|---|---|---|---|---|---|---|---|---|---|---|---|---|---|
| | TZM-bI | | PBMC | DC/T4 | Ba-L | | VI829 | | L100I+ | | Ba-L | | VI829 | | |
| Cpd | Ba-L | VI829 | Ba-L | Ba-L | V106A | FC | Y181C | FC | K103N | FC | * | FC | ** | FC | TZM-bI |

TMC125

TMC278

DATA

The Partition Coefficient (Log D)

10 mM stock solution (in DMSO) was prepared.

200 μM solution (in DMSO) was prepared from 10 mM stock solution.

A set of 5-10 dilutions (in MeOH) of each compound were prepared from 200 μM solution to give final test concentrations between 1 nm and 2 μM.

MS tuning was done for each compound to find the daughter peaks using 500 nm solution.

Calibration curve was made for each compound to evaluate the linearity of our method.

Octanol was first saturated with PBS and PBS was first saturated with octanol

20 μl of a 10 mM DMSO stock solution was added to 990 μl of PBS (pH 7.4) and then 990 μl of octanol was added. The experiment was done in duplicate. After two hours of shaking at 37° C. and keeping at room temperature for 30 minutes the two layers were separated. After separation, octanol layer was diluted further with MeOH and compound was quantified in both layers by UPLC (waters). The samples were analysed in triplicate.

$$\log D = \log\left[\left(\frac{Conc_{INITIAL} - Conc_{FINAL}}{Conc_{FINAL}}\right) \times \left(\frac{V_{aq}}{V_{oct}}\right)\right]$$

Where:

Conc$_{INITIAL}$=Concentration of compound in the initial aqueous solution (PBS)

Conc$_{FINAL}$=Concentration of compound in final aqueous phase (PBS)

V$_{aq}$=Volume of aqueous (PBS)

V$_{oct}$=Volume of octanol

The log D values for TMC120 and TMC278 are >5 and 4.0. In case of our target compound T2 the value is 3.8. T2 is less lipophilic than TMC120. Based on this log D result we can postulate that the described compounds under this invention can have improved formulation properties.

REFERENCES

1. Evolution of anti-HIV drug candidates. Part 2: Diaryltriazine (DATA) analogues. Ludovici, D. W.; Kavash, R. W.;

Kukla, M. J.; Ho, C. Y.; Ye, H.; De Corte, B. L.; Andries, K.; de Bethune, M. P.; Azijn, H.; Pauwels, R.; Moereels, H. E.; Heeres, J.; Koymans, L. M.; de Jonge, M. R.; Van Aken, K. J.; Daeyaert, F. F.; Lewi, P. J.; Das, K.; Arnold, E.; Janssen, P. A. Bioorg. Med. Chem. Lett. 2001, 11, 2229-34.
2. Trisubstituted 1,3,5-triazine derivatives for treatment of HIV infections. Daeyaert, F. F. D.; De Corte, B.; De Jonge, M. R.; Heeres, J.; Ho, C. Y.; Janssen, P. A. J.; Kavash, R. W.; Koymans, L. M. H.; Kukla, M. J.; Ludovici, D. W. WO 99/50256.
3. Trisubstituted 1,3,5-triazine derivatives for treatment of HIV infections. Kukla, M. J.; Ludovici, D. W.; Kavash, R. W.; Heeres, J.; Janssen, P. A. J. EP 0 945 447 A1.
4. HIV replication inhibitors. Kukla, M. J.; Ludovici, D. W.; Kavash, R. W.; De Corte, B. L. D.; Heeres, J.; Janssen, P. A. J.; Koymans, L. M. H.; De Jonge, M. R.; Van Aken, K. J. A.; Krief, A.; Leenders, R. G. G. WO 2001/85700.
5. HIV replication inhibiting pyrimidines and triazines. Guillemont, J. E. G.; Pasquier, E. T, J.; Heeres, J.; Hertogs, K.; Bettens, E.; Lewi, P. J.; De Jonge, M. R. Koymans, L. M. H.; Daeyaert, F. F. D.; Vinkers, H. M. WO 2004/074262.
6. Microbicidal pyrimidine or triazine for preventing sexual HIV transmission. Van Roey, J. M.; De Bethune, M. T. M. M. G.; Stoffels, P. WO 2003/094920 and US 2011/0165093.

The invention claimed is:

1. A compound represented by Formula (Ia) or (Ib) or a stereoisomer, tautomer, racemic, salt, hydrate, or solvate thereof,

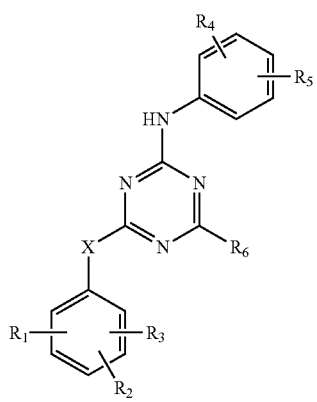
(Ia)

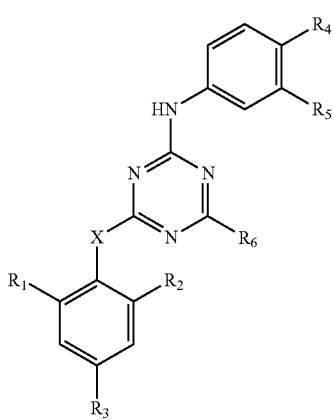
(Ib)

Wherein
$R_1$, $R_2$, and $R_3$ are each independently selected from the group consisting of —$C_{1-6}$alkyl, -halo, and —CH=CH—CN;
$R_4$ and $R_5$ are each independently selected from the group consisting of —H, —CN, and —CH=CH—CN;
$R_6$ is selected from the group consisting of —H, and —$NR_7R_8$;
$R_7$ and $R_8$ are each independently selected from the group consisting of —H, —$C_{1-6}$alkyl, and -phenyl; said -phenyl being optionally substituted with —CN; or
$R_7$ and $R_8$ taken together with the N atom to which they are attached form a 5- or 6-membered heterocycle comprising from 1 to 3 heteroatoms selected from N, S and O;
X is selected from the group consisting of —NH—, —$NC_{1-6}$alkyl-, —O—; and
wherein at least one of $R_1$-$R_5$ is —CH=CH—CN.

2. A compound according to claim 1 wherein
$R_1$ and $R_2$ are each independently selected from the group consisting of —$C_{1-6}$alkyl, and -halo;
$R_3$ is —CH=CH—CN;
$R_4$ and $R_5$ are each independently selected from the group consisting of —H, and —CN;
$R_6$ is selected from the group consisting of —H, and —$NR_7R_8$;
$R_7$ and $R_8$ are each independently selected from the group consisting of —H, —$C_{1-6}$alkyl, and -phenyl; said -phenyl being optionally substituted with —CN; or
$R_7$ and $R_8$ taken together with the N atom to which they are attached form a 5- or 6-membered heterocycle comprising from 1 to 3 heteroatoms selected from N, S and O;
X is selected from the group consisting of —NH—, —$NC_{1-6}$alkyl-, —O—.

3. A compound according to claim 1 wherein
$R_1$, $R_2$, and $R_3$ are each independently selected from the group consisting of —$C_{1-6}$alkyl, -halo, and —CH=CH—CN;
$R_4$ and $R_5$ are each independently selected from the group consisting of —H, and —CN;
$R_6$ is —$NR_7R_8$;
$R_7$ and $R_8$ are each independently selected from the group consisting of —H, —$C_{1-6}$alkyl, and -phenyl; said -phenyl being optionally substituted with —CN; or
$R_7$ and $R_8$ taken together with the N atom to which they are attached form a 5- or 6-membered heterocycle comprising from 1 to 3 heteroatoms selected from N, S and O;
X is selected from the group consisting of —NH—, —$NC_{1-6}$alkyl-, —O—; and
wherein at least one or $R_1$-$R_3$ is —CH=CH—CN.

4. A compound according to claim 1 wherein
$R_1$ and $R_2$ are each independently selected from the group consisting of —$C_{1-6}$alkyl, and -halo;
$R_3$ is —CH=CH—CN;
$R_4$ and $R_5$ are each independently selected from the group consisting of —H, —CN, and —CH=CH—CN;
$R_6$ is —$NR_7R_8$;
$R_7$ and $R_8$ are each independently selected from the group consisting of —H, —$C_{1-6}$alkyl, and -phenyl; said -phenyl being optionally substituted with —CN; or
$R_7$ and $R_8$ taken together with the N atom to which they are attached form a 5- or 6-membered heterocycle comprising from 1 to 3 heteroatoms selected from N, S and O;
X is selected from the group consisting of —NH—, —$NC_{1-6}$alkyl-, and —O—.

5. A compound according to claim 1 wherein
$R_1$ and $R_2$ are each independently selected from the group consisting of —$C_{1-6}$alkyl, and -halo;
$R_3$ is —CH=CH—CN;
$R_4$ is —CN;
$R_5$ is —H;
$R_6$ is —$NR_7R_8$;
$R_7$ and $R_8$ are each independently selected from the group consisting of —H and —$C_{1-6}$alkyl;
X is selected from the group consisting of —NH— and —O—.

6. A compound according to claim 1 wherein the compound is the E-isomer.

7. A pharmaceutical composition comprising a compound according to claim 1.

8. A method of inhibiting HIV reverse transcriptase comprising administering to a subject in need thereof an effective amount of a compound according to claim 1.

9. A method of treating HIV infection comprising administering to a subject in need thereof an effective amount of a compound according to claim 1.

10. A method of treating HIV infection in a subject in need thereof, comprising administering to said subject an effective amount of a composition according to claim 7.

11. A method of inhibiting HIV reverse transcriptase comprising administering to a subject in need thereof an effective amount of a composition according to claim 7.

* * * * *

UNITED STATES PATENT AND TRADEMARK OFFICE
CERTIFICATE OF CORRECTION

| | | |
|---|---|---|
| PATENT NO. | : 9,650,348 B2 | |
| APPLICATION NO. | : 14/385843 | |
| DATED | : May 16, 2017 | |
| INVENTOR(S) | : Jan Heeres et al. | |

It is certified that error appears in the above-identified patent and that said Letters Patent is hereby corrected as shown below:

Column 2, Line 1:
"DATA's is that they are less active or even ineffective"
Should read:
--DATAs is that they are less active or even ineffective--;

Column 2, Line 11:
"NNRTI's, which are currently used in clinical management"
Should read:
--NNRTIs, which are currently used in clinical management--;

Column 5, Lines 54-55:
"The terms "heterocycle" as used herein by itself or as part of another group refer to non-aromatic, fully saturated or"
Should read:
--The term "heterocycle" as used herein by itself or as part of another group refers to non-aromatic, fully saturated or--;

Column 6, Line 11:
"tetrahydrofuranyl, tetrehydrothienyl, tetrahydroquinolinyl"
Should read:
--tetrahydrofuranyl, tetrahydrothienyl, tetrahydroquinolinyl--;

Column 11, Line 60:
"between 0.01 to 1000 mg per kilogram body weight day of"
Should read:
--between 0.01 to 1000 mg per kilogram body weight of--;

Signed and Sealed this
Twenty-fourth Day of April, 2018

Andrei Iancu
*Director of the United States Patent and Trademark Office*

CERTIFICATE OF CORRECTION (continued)
U.S. Pat. No. 9,650,348 B2

Column 11, Line 63:
"50, 100, 150, 200 or 250 mg, per kilogram body weight day"
Should read:
--50, 100, 150, 200 or 250 mg, per kilogram body weight--;

Column 15:

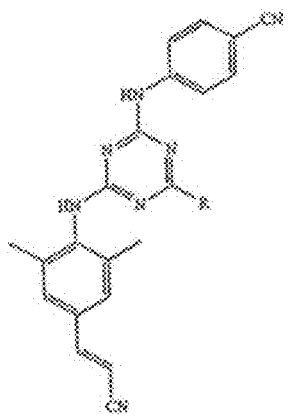

" R₄ = amino, subst. amino "

Should read:

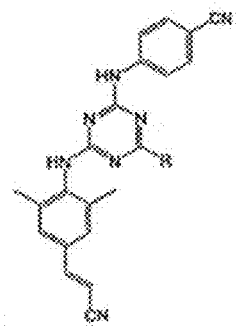

-- R = amino, subst. amino --;

Column 19:

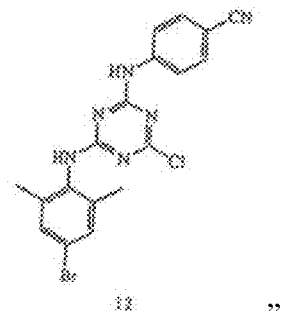

"  R  "

Should read:

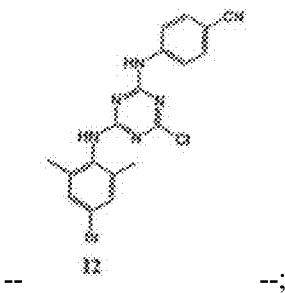
Column 21, Line 26:
"The above compound was prepared from 14 using the"
Should read:
--The above compound was prepared from I4 using the--;
Column 23:
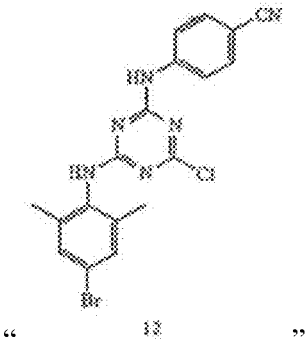
Should read:
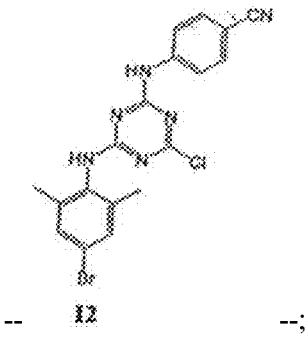
Column 24, Line 60:
"The above compound was prepared from 18 using the"
Should read:
--The above compound was prepared from I8 using the--;
Column 26, Line 53:

"The above compound was prepared from 110 using the"
Should read:
--The above compound was prepared from I10 using the--;

Column 29, Line 7:
"$^1$H NMR (DMSO-d6, 400 MHz) δ 7.85 (br s, 2H), 7.61"
Should read:
--$^1$H NMR (DMSO-d$_6$, 400 MHz) δ 7.85 (br s, 2H), 7.61--;

Column 29, Line 17:
"$^1$H NMR (MeOD), 400 MHz) δδ 8.0 (br s, 1H), 7.65 (m,"
Should read:
--$^1$H NMR (MeOD), 400 MHz) δ 8.0 (br s, 1H), 7.65 (m,--;

Column 30, Line 18:
"$^1$H NMR (DMSO-d6, 400 MHz) δ 10.1 (s, 1H), 7.78-7.63"
Should read:
--$^1$H NMR (DMSO-d$_6$, 400 MHz) δ 10.1 (s, 1H), 7.78-7.63--;

Column 30:

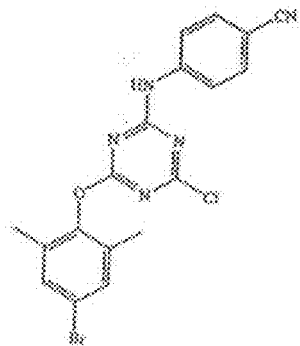

" "

Should read:

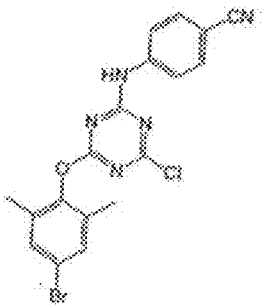

-- I14 --;

Column 32, Line 66:

"

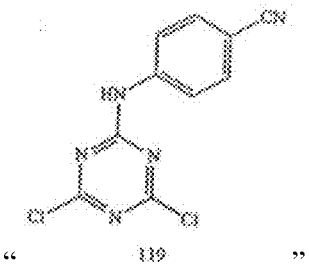

"

Should read:

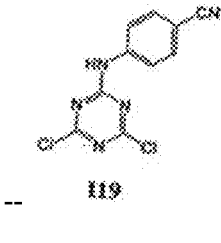

--      119      --;

Column 34, Line 8:
"chromatography using 90 EtOAc in hexanes afforded white"
Should read:
--chromatography using 90% EtOAc in hexanes afforded white--;

Column 35, Line 2:
"reader (BioRad, Tokio, Japan). Each compound was tested"
Should read:
--reader (BioRad, Tokyo, Japan). Each compound was tested--;

Column 36, Line 7:
"safety and effectiveness for prevention of HIV in african"
Should read:
--safety and effectiveness for prevention of HIV in African--;

Column 36, Table 2:
"** = L100I + E138K + T369I"
Should read:
-- = L100I + E138K + T369I**--; and Column 39, Line 20:
"Guillemont, J. E. G.; Pasquier, E. T, J.; Heeres, J.;"
Should read:
--Guillemont, J. E. G.; Pasquier, E. T. J.; Heeres, J.;--.